US008926989B2

(12) United States Patent
Burbelo et al.

(10) Patent No.: US 8,926,989 B2
(45) Date of Patent: Jan. 6, 2015

(54) COMPOSITIONS AND METHODS FOR SCREENING FOR LYME DISEASE

(75) Inventors: Peter D. Burbelo, Washington, DC (US); Adriana Marques, Potomac, MD (US); Michael J. Iadarola, Washington, DC (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/583,472

(22) PCT Filed: Mar. 10, 2011

(86) PCT No.: PCT/US2011/027888
§ 371 (c)(1),
(2), (4) Date: Nov. 13, 2012

(87) PCT Pub. No.: WO2011/112805
PCT Pub. Date: Sep. 15, 2011

(65) Prior Publication Data
US 2013/0164759 A1 Jun. 27, 2013

Related U.S. Application Data

(60) Provisional application No. 61/312,520, filed on Mar. 10, 2010.

(51) Int. Cl.

| | |
|---|---|
| ***A61K 39/02*** | (2006.01) |
| ***A61K 39/00*** | (2006.01) |
| ***A61K 39/116*** | (2006.01) |
| ***A61K 38/00*** | (2006.01) |
| ***C07K 1/00*** | (2006.01) |
| ***C07H 21/04*** | (2006.01) |
| ***G01N 33/569*** | (2006.01) |
| ***G01N 33/68*** | (2006.01) |

(52) U.S. Cl.
CPC ...... *G01N 33/56911* (2013.01); *G01N 33/6854* (2013.01); *G01N 2333/20* (2013.01); *Y10S 530/825* (2013.01); *Y10S 435/975* (2013.01)
USPC .................. 424/234.1; 424/192.1; 424/190.1; 424/203.1; 424/184.1; 514/1.1; 530/350; 530/300; 530/825; 536/23.7; 435/975

(58) Field of Classification Search
CPC .................... G01N 2333/20; G01N 33/56911; G01N 33/6854
See application file for complete search history.

(56) References Cited

U.S. PATENT DOCUMENTS

| | | | | |
|---|---|---|---|---|
| 6,719,983 | B2 | 4/2004 | Norris et al. | |
| 2003/0092903 | A1 * | 5/2003 | Norris et al. | 536/23.7 |
| 2011/0294147 | A1 | 12/2011 | Burbelo et al. | |

FOREIGN PATENT DOCUMENTS

WO WO-2004/058181 A2 7/2004

OTHER PUBLICATIONS

Bacon et al., "Serodiagnosis of Lyme Disease by Kinetic Enzyme-Linked Immunosorbent Assay Using Recombinant V1sE1 or Peptide Antigens of Borrelia burgdorferi Compared with 2-Tiered Testing Using Whole-Cell Lysates", Journal of Infectious Disease, vol. 187, No. 15, pp. 1187-1199 (2003).
Burbelo et al., "Rapid, Simple, Quantitative, and Highly Sensitive Antibody Detection for Lyme Disease", Clinical and Vaccine Immunology, vol. 17, No. 6, pp. 904-909 (2010).

* cited by examiner

*Primary Examiner* — S. Devi
(74) *Attorney, Agent, or Firm* — Edwards Wildman Palmer LLP; Peter F. Corless

(57) ABSTRACT

The invention provides compositions, methods, and kits for the diagnosis or detection of infection by a pathogen that causes Lyme disease in a subject.

6 Claims, 5 Drawing Sheets

Figure 4

```
A  VOVO antigens
Bb          MKKDDQIAAAIALRGMAKDGKFAVKELTSPVVAESPKKPMKKDDQ
            IAAAMVLRGMAKDGQFALKPVVAESPKKP (SEQ ID NO: 1)

Bg          CMKKDDQIAAAMVLRGMAKDGQFALKPVVAESPKKPCMKKDDQI
            AAAMVLRGMAKDGQFALKPVVAESPKKP (SEQ ID NO: 2)

Ba          CMKKSDKIAAAIVLRGVAKSGKFAVAPVVAESPKKPCMKKRND
            KIVAAIVLRGVAKDGKFAAAPVVAESPKKP (SEQ ID NO: 3)

B           "V" peptides
Bb-VlsE-Δ1  -MKK-DDQIAAAIALRGMAKDGKFAVKE 26   (SEQ ID NO: 4)
Bb-VlsE-Δ2  -MKK-DDQIAAAMVLRGMAKDGQFALK- 25   (SEQ ID NO: 5)
Bg-VlsE     CMKK-DDQIAAAMVLRGMAKDGQFALK- 26   (SEQ ID NO: 6)
Ba-VlsE     CMKK-SDKIAAAIVLRGVAKSGKFAVA- 26   (SEQ ID NO: 7)
Ba-VlsE(2)  CMKKRNDKIVAAIVLRGVAKDGKFAAA- 27   (SEQ ID NO: 8)
             ***  .*:*.**:.***:**.*:**

Bb-VlsE-Δ1  -MKKDDQIAAAIALRGMAKDGKFAVKE 26
Bb-VlsE-Δ2  -MKKDDQIAAAMVLRGMAKDGQFALK- 25
Bg-VlsE      CMKKDDQIAAAMVLRGMAKDGQFALK- 26
              **********:.********:**:*

Bb-VlsE-Δ1  -MKKDDQIAAAIALRGMAKDGKFAVKE 26
Bb-VlsE-Δ2  -MKKDDQIAAAMVLRGMAKDGQFALK- 25
Ba-VlsE     CMKKSDKIAAAIVLRGVAKSGKFAVA- 26
             ***.*:****:.***:**.*:**:

Bb-VlsE-Δ1  -MKK-DDQIAAAIALRGMAKDGKFAVKE 26
Bb-VlsE-Δ2  -MKK-DDQIAAAMVLRGMAKDGQFALK- 25
Ba-VlsE(2)   CMKKRNDKIVAAIVLRGVAKDGKFAAA- 27
              ***  :*:*.**:.***:****:**

C           "O" peptide
OspC                          PVVAESPKKP (SEQ ID NO: 9)
```

```
                    FLAG epitope                  Ruc
atcagccgccacc atggactacaaggacgacgatgacaagggatctacttcgaaa..  (10)
              M   D   Y   K   D   D   D   D   K   G   S   T   S   K...  (11)

            BamHI EcoRI     HindIII XhoI       XbaI
aaaaatgaacaaggatccgaattcaaaaagcttctcgagagtacttctagagcg      (12)
K  N  E  Q  G  S  E  F  K  K  L  L  E  S  T  S  R  A        (13)
```

COMPOSITIONS AND METHODS FOR SCREENING FOR LYME DISEASE

INCORPORATION BY REFERENCE

This application is a 35 U.S.C §371 U.S. national entry of Intenational Application PCT/US2011/027888(WO 2011/112805) having an International filing date of Mar. 10, 2011, which claims the benefit of U.S. Provisional Application Ser.No. 61/312,520, filed Mar.10, 2010, the contents of which are incorporated herein by reference in their entirety.

This application claims the benefit of U.S. Provisional Application Ser. No. 61/312,520 filed Mar. 10, 2010, the contents of which is incorporated herein by reference in its entirety.

SEQUENCE LITSTIONG

The instant application contains a Sequence Listing which has been submitted electronically in ASCII format and is hereby incorporated by reference in its entirety. Said ASCII copy, created on Jan. 28, 2014, is named 85313US(47992)_SL.txt and is 33,555 bytes in size.

GOVERNMENT SUPPORT

This work was supported by the Intramural Research Program of the National Institutes of Health, the National Institute of Dental and Craniofacial Research, the NIH Clinical Center, and the National Institute for Allergy and Infectious Disease. The Government has certain rights to this invention.

BACKGROUND

Lyme disease is caused by the spirochete *Borrelia burgdorferi* (Bb) in North America and predominantly by *Borrelia afzelii* and *Borrelia garinii* in Eurasia. The pathogen is transmitted by the bite of a tick (*Ixodes* sp.), deer tick or western black-legged tick in North America. One of the typical first signs of *Borrelia* sp. infection is erythema migrans (EM), a bull's eye-like skin lesion, which arises within a few days of the bite. However, the bite may not be painful, and a rash does not develop in all patients. Patients can also experience flu-like symptoms, however, such symptoms may be attributed by the patient to any of a number of other causes.

After infection, the spirochetes can disseminate in the bloodstream to various target tissues. Prompt treatment with antibiotics can typically kill the pathogen and prevent long term ill effects of infection. If the infection is not treated, or not successfully treated, it can result in neurological, rheumatological, and cardiac damage over time. Some common symptoms from long-term Lyme infection include arthritis, facial palsy, and neuroboreliosis. Even after antibiotic treatment of Lyme disease, some individuals show post-Lyme disease syndrome (PLDS) and have lingering symptoms such as fatigue, musculoskeletal pain, and cognitive complaints.

Because of the difficulty in culturing *Borrelia* bacteria in the laboratory, diagnosis of Lyme disease is typically based on clinical exam findings and a history of exposure to endemic Lyme areas (Ryan K J, Ray C G (editors) 2004. *Sherris Medical Microbiology* (4th ed.). McGraw Hill. pp. 434-437). The EM rash, which does not occur in all cases, is considered sufficient to establish a diagnosis of Lyme disease even when serologic blood tests are negative (Hofmann et al., 1996, *Infection* 24: 470-472.; Pachner et al., 1989. *Rev. Infect. Dis.* 11 Suppl 6: S1482-1486). Serological testing can be used to support a clinically suspected case but is not diagnostic by itself (Ryan K J, Ray C G (editors) 2004. *Sherris Medical Microbiology* (4th ed.). McGraw Hill. pp. 434-437).

SUMMARY OF THE INVENTION

The invention provides compositions, methods, and kits for the detection of infection by a *Borrelia* sp. pathogen.

The invention provides compositions containing an isolated peptide having an amino acid sequence at least 70% identical, at least 80% identical, at least 90% identical, or at least 95% identical to SEQ ID NO: 1, wherein a 10-fold molar excess of the peptide inhibits binding of at least 50% of a peptide comprising the amino acid sequence of SEQ ID NO: 1 to a sample from a subject suffering from an infection by *Borrelia burgdorferi*. In certain embodiments, the isolated peptide has the amino acid sequence of SEQ ID NO: 1. A sample from a subject suffering from infection by *Borrelia burgdorferi, Borrelia afzelii, Borrelia garinii*, and/or *Borrelia valaisiana* can be evaluated using these compositions in routine diagnostic methods such as those provided herein. In embodiments, the subject is suffering from *Borrelia burgdorferi.*

The invention provides compositions that include the mixtures of the antigenic components of SEQ ID NO: 1. Such compositions according to the invention contain one or more (e.g., 1, 2, 3, 4, 5, 6, 7, 8, 9, 10, etc) isolated peptides, wherein the peptides include amino acid sequences of SEQ ID NO: 4, SEQ ID NO: 5, and SEQ ID NO: 9. The mixtures can include separate peptides having the sequences of SEQ ID NO: 4, SEQ ID NO: 5, and SEQ ID NO: 9. The peptides can have sequences of SEQ ID NO: 4, SEQ ID NO: 5, and SEQ ID NO: 9 joined, for example, by covalent linkage, such as a peptide bond or a peptide linker. A sample from a subject suffering from infection by *Borrelia burgdorferi, Borrelia afzelii*, and/or *Borrelia garinii* can be evaluated using these compositions in routine diagnostic methods such as those provided herein. In embodiments, the subject is suffering from *Borrelia burgdorferi.*

The invention provides compositions containing an isolated peptide having an amino acid sequence at least 70% identical, at least 80% identical, at least 90% identical, or at least 95% identical to SEQ ID NO: 3, wherein a 10-fold molar excess of the peptide inhibits binding of at least 50% of a peptide comprising the amino acid sequence of SEQ ID NO: 3 to a sample from a subject suffering from an infection by *Borrelia afzelii*. In certain embodiments, the isolated peptide has the amino acid sequence of SEQ ID NO: 3. A sample from a subject suffering from infection by *Borrelia burgdorferi, Borrelia afzelii, Borrelia garinii*, and/or *Borrelia valaisiana* can be evaluated using these compositions in routine diagnostic methods such as those provided herein. In embodiments, the subject is suffering from *Borrelia afzelii.*

The invention provides compositions that include the mixtures of the antigenic components of SEQ ID NO: 3. Such compositions according to the invention contain one or more (e.g., 1, 2, 3, 4, 5, 6, 7, 8, 9, 10, etc) isolated peptides, wherein the peptides include amino acid sequences of SEQ ID NO: 7, SEQ ID NO: 8, and SEQ ID NO: 9. The mixtures can include separate peptides having the sequences of SEQ ID NO: 7, SEQ ID NO: 8, and SEQ ID NO: 9. The peptides can have sequences of SEQ ID NO: 7, SEQ ID NO: 8, and SEQ ID NO: 9 joined, for example, by covalent linkage, such as a peptide bond or a peptide linker. A sample from a subject suffering from infection by *Borrelia burgdorferi, Borrelia afzelii, Borrelia garinii*, and/or *Borrelia valaisiana* can be evaluated using these compositions in routine diagnostic methods such as those provided herein. In embodiments, the subject is suffering from *Borrelia afzelii.*

The invention provides compositions containing an isolated peptide having an amino acid sequence at least 70% identical, at least 80% identical, at least 90% identical, or at least 95% identical to SEQ ID NO: 2, wherein a 10-fold molar excess of the peptide inhibits binding of at least 50% of a peptide comprising the amino acid sequence of SEQ ID NO: 2 to a sample from a subject suffering from an infection by *Borrelia garinii*. In certain embodiments, the isolated peptide has the amino acid sequence of SEQ ID NO: 2. A sample from a subject suffering from infection by *Borrelia burgdorferi, Borrelia afzelii, Borrelia garinii*, and/or *Borrelia valaisiana* can be evaluated using these compositions in routine diagnostic methods such as those provided herein. In embodiments, the subject is suffering from *Borrelia garinii.*

The invention provides compositions that include the mixtures of the antigenic components of SEQ ID NO: 2. Such compositions according to the invention contain one or more (e.g., 1, 2, 3, 4, 5, 6, 7, 8, 9, 10, etc) isolated peptides, wherein the peptides include amino acid sequences of SEQ ID NO: 6 and SEQ ID NO: 9. The mixtures can include separate peptides having the sequences of SEQ ID NO: band SEQ ID NO: 9. The peptides can have sequences of SEQ ID NO: 6 and SEQ ID NO: 9 joined, for example, by covalent linkage, such as a peptide bond or a peptide linker. A sample from a subject suffering from infection by *Borrelia burgdorferi, Borrelia afzelii*, and/or *Borrelia garinii* can be evaluated using these compositions in routine diagnostic methods such as those provided herein. In embodiments, the subject is suffering from *Borrelia garinii.*

The invention provides compositions that include the mixtures of the antigenic peptide sequences provided herein. Such compositions according to the invention contain one or more (e.g., 1, 2, 3, 4, 5, 6, 7, 8, 9, 10, etc) isolated peptides, wherein the peptides include amino acid sequences of SEQ ID NO: 1-9. The mixtures can include separate peptides having the sequences of SEQ ID NO: 1-9. The peptides can have sequences of SEQ ID NO: 1-9 joined, for example, by covalent linkage, such as a peptide bond or a peptide linker. A sample from a subject suffering from infection by *Borrelia burgdorferi, Borrelia afzelii, Borrelia garinii*, and/or *Borrelia valaisiana* can be evaluated using these compositions in routine diagnostic methods such as those provided herein.

The isolated peptides can further be linked to other polypeptide sequences by linkages well-known in the art, including but not limited to, chemical linkers, peptide bonds, and peptide linkers. For example, peptides of the invention can be linked to one or more of reporter polypeptide sequences and/or an epitope tag sequences. In certain embodiments, one of the peptides of SEQ ID NO: 1-9 is joined to a reporter polypeptide sequence(s) and/or an epitope tag sequence(s). In certain embodiments, 2, 3, 4, 5, 6, 7, 8, or 9 of peptides having the sequence of SEQ ID NO: 1-9 are joined to a reporter polypeptide sequence(s) and/or an epitope tag sequence(s).

The invention provides nucleic acids encoding one or more of the peptides (1, 2, 3, 4, 5, 6, 7, 8, or 9) of the invention, alone or in a mixture with other nucleic acids encoding one or more polypeptides of the invention. In certain embodiments, each of the peptides is encoded by a separate nucleic acid expression construct. In certain embodiments, more than one peptide is encoded by a single nucleic acid expression construct.

The invention provides methods for diagnosing infection by *Borrelia* sp. in a subject including the steps of:

a) obtaining a sample from a subject, b) contacting the sample with the peptide composition of any one of the antigenic peptide compositions of the invention, and c) detecting binding of the peptide to an antibody in the sample, wherein binding is indicative of infection of the subject by *Borrelia* sp.

The invention also provides methods for monitoring therapeutic treatment response in a subject having a *Borrelia* sp. infection including the steps of:

a) obtaining a sample from a subject after therapeutic treatment, b) contacting the sample with the peptide composition of any one of the antigenic peptide compositions of the invention, and c) detecting binding of the peptide to an antibody in the sample, and d) correlating binding with the treatment response of the subject, thereby evaluating the therapeutic treatment response of the subject. In embodiments, the therapeutic treatment involves the administration of an immunogenic composition (e.g., a vaccine).

The invention also provides methods for selecting a treatment regimen for a subject having a *Borrelia* sp. infection including the steps of:

a) administering an agent to a subject, b) obtaining a sample from the subject, c) contacting the sample with the peptide composition of any one of the antigenic peptide compositions of the invention, and d) detecting binding of the peptide to an antibody in the sample, wherein decreased binding is indicative that the subject is susceptible to treatment with the agent, and wherein the treatment regimen comprises administering the agent to the subject if the subject is determined to be susceptible to treatment with the agent.

In the above aspects of the invention, detection of binding of the peptide and the antibody can be assayed for by any method well-known in the art. In embodiments, detection includes detection of an enzymatic reaction. Enzymatic reactions can be catalyzed by an enzyme, for example, luciferase, alkaline phosphatase, or beta-galactosidase. In certain embodiments, the methods include isolating the antibody-antigen complex from the sample, for example by binding the antigen-antibody complex to a solid substrate. In certain embodiments, the antibody-antigen complex is formed in solution. In embodiments, the assay is an immunoassay. Immunoassays include, but are not limited to, competitive and non-competitive assay systems using techniques such as LIPS, BIAcore analysis, FACS analysis, immunofluorescence, immunocytochemistry, Western blots, radioimmunoassays, ELISA, “sandwich” immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays. See Ausubel et al, eds, 1994, Current Protocols in Molecular Biology, Vol. 1, John Wiley & Sons, Inc., New York, which is hereby incorporated by reference.

In the above aspects of the invention, the sample can be any body fluid or tissue from the subject. Samples can be obtained from the subject using any method well-known in the art. In embodiments, the sample is blood, plasma, or serum. In embodiments, the sample is donated blood, tissue, or organ.

The invention provides kits including one or more peptides of the invention. The invention also provides kits including one or more nucleic acids for encoding one or more peptides of the invention. In embodiments, the kits further include instructions for using the peptides and/or nucleic acids in any of the methods described herein.

The invention further provides other embodiments that are provided herein.

BRIEF DESCRIPTION OF THE FIGURES

FIG. 3A includes a scatter plot showing the results from 141 serum samples from patients with confirmed Lyme disease, and 59 control serum samples. Each symbol represents a serum sample from an individual patient. Using the cut-off based on the mean plus 5 SD shown by the solid line, the VOVO LIPS test showed 94% sensitivity and 100% specificity. The C6 ELISA on these same samples showed 76% sensitivity and 96% specificity FIG. 3B includes a plot showing the correlation between the titer values obtained from LIPS and C6 ELISA. The LIPS titer values were first $\log^{10}$ transformed and then analyzed using a Speraman rank correlation. These results showed rs=0.778.

FIGS. 4A-4C include sequences from *Borrelia* sp. FIG. 4A includes sequences showing three exemplary VOVO antigens for *Borrelia burgdorferi* (Bb, SEQ ID NO: 1), *Borrelia garinii* (Bg, SEQ ID NO: 2), and *Borrelia afzelii* (Ba, SEQ ID NO: 3). FIG. 4B includes sequence alignments of VslE ("V" fragments) peptide sequences from *Borrelia burgdorferi* (Bb SEQ ID NO: 4 and 5), *Borrelia garinii* (Bg, SEQ ID NO: 6), and *Borrelia afzelii* (Ba, SEQ ID NO: 7 and 8). Alignments shows sequence homology within the group of sequences and pairwise homology between pairs of sequences. FIG. 4C includes a sequence fragment of the OspC ("O" fragment) peptide present in *Borrelia burgdorferi, Borrelia garinii*, and *Borrelia afzelii* (SEQ ID NO: 9). FIG. 4B discloses SEQ ID NOS 4-8, 4-6, 4-5, 7, 4-5 and 8,respectived, in order of appearance.

DEFINITIONS

Figure 1:
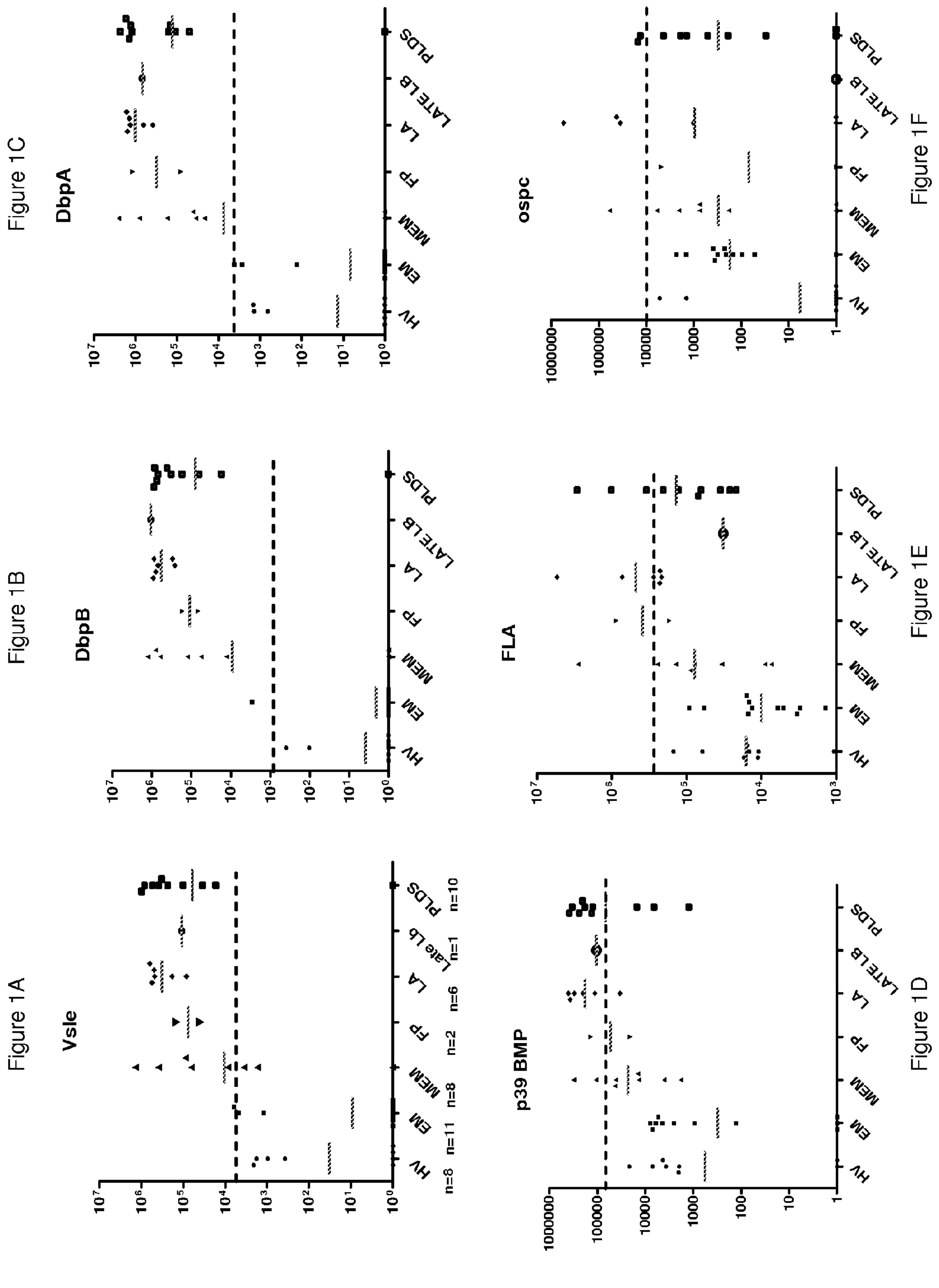
FIGS. 1A-1F include scatter plots showing the antibody titers resulting from VlsE-Δ1 (FIG. 1A), DbpB (FIG. 1B), DbpA (FIG. 1C), p39 (BMP) (FIG. 1D), Fla (FIG. 1E) and OspC (FIG. 1F) tested by LIPS. The serum samples included 11 EM (erythema migrans), 8 multiple erythema migrans (MEM), 2 Lyme palsy, 6 Lyme arthritis, 1 late Lyme neuroborreliosis, post-Lyme disease syndrome (PLDS) patient samples and 8 uninfected control samples. Each symbol represents a serum sample from an individual patient. The geometric mean is shown as the bar. The cut-off value for calculating sensitivity and specificity is shown by the dotted line and is derived from the mean plus 5 standard deviation (SD) of the 8 uninfected controls.

"Antigenic fragment" and the like are understood as at least that portion of an antigen capable of being recognized and specifically bound by an antibody present in a subject having or suspected of having an infection, particularly a *Borrelia* sp., particularly when the antigen includes a partial sequence of consecutive amino acids of at least one of VslE and OspC antigens. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. Typically, antigenic fragments include at least 3, and more usually, at least 4, 5, 6, 7, 8, or 10 amino acids in a unique spatial conformation. Moreover, common epitopes for antigens have been mapped and can be used as antigenic fragments in the compositions and methods provided herein. Antigenic fragments can include deletions of the amino acid sequence from the N-terminus or the C-terminus, or both. For example, an antigenic fragment can have an N- and/or a C-terminal deletion of about 1, 2, 3, 4, 5, 6, 7, 8, 9, 10, 15, 20, 25, 30, 35, 40, 45; 50, 55, 60, 65, 70, 75, 80, 85, 90, 95, 100, 110, 120, 130, 140, 150, or more amino acids. Antigenic fragments can also include one or more internal deletions of the same exemplary lengths. Antigenic fragments can also include one or more point mutations, particularly conservative point mutations. In addition, an antigenic fragment (e.g., a protein) can include the full length, wild-type sequence of the antigen. An antigenic fragment can include more than one potential antibody binding site.

As used herein, "binding" is understood as having at least a $10^2$ or more, $10^3$ or more, preferably $10^4$ or more, preferably $10^5$ or more, preferably $10^6$ or more preference for binding to a specific binding partner as compared to a non-specific binding partner (e.g., binding an antigen to a sample known to contain the cognate antibody). That an antibody "specifically binds" to an antigen, epitope or protein means that the antibody reacts or associates more frequently, more rapidly, with greater duration, with greater affinity, or with some combination of the above to an antigen, epitope or protein than with alternative substances, including unrelated proteins.

As used herein, "*Borrelia* sp." is understood as any *Borrelia* species known to cause Lyme disease, for example, *Borrelia burgdorferi* (Bb), *Borrelia afzelii, Borrelia garinii*, and *Borrelia valaisiana.*

As used herein, "changed as compared to a control" sample or subject is understood as having a level of the analyte or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g, β-galactosidase or luciferase). Depending on the method used for detection the amount and measurement of the change can vary. Changed as compared to a control reference sample can also include a change in one or more signs or symptoms associated with or diagnostic of *Borrelia* sp. infection. Determination of statistical significance is within the ability of those skilled in the art, e.g., the number of standard deviations from the mean that constitute a positive result.

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. As used herein in reference to antigenic polypeptides, "consisting essentially of" is understood as an antigenic polypeptide sequence including the claimed sequence, and optionally further containing other elements or optionally having shorter amino acid sequences than presented that do not materially affect the basic and novel characteristics of the antigenic polypeptide. That is, other elements or deletion of sequences that neither substantially inhibit or enhance binding of the peptide to cognate antibodies in a subject sample, or decrease the specificity of the binding of the antigen to a subject sample. In certain embodiments, antigenic fragments of longer polypeptides can be expressed to include an initiator methionine, a signal sequence for translocation of the protein, or may include sequences at the N- or C-terminus after cleavage with a protease not present in the native sequence. As used herein, a polypeptide consisting essentially of an antigenic fragment can be linked covalently (e.g., by a peptide bond or other linkage) to a second polypeptide, for example a reporter polypeptide, or an epitope tag (e.g., a FLAG tag). In an antigen with multiple domains or binding sites, the antigenic domains can be covalently linked by any type of linkage that does not disrupt binding to the antigenic site, e.g., through any of a number of chemical covalent linkages (e.g., cross-linking reagents commercially available from Pierce, a part of Thermo Fisher Scientific, and other sources), or through peptide bonds, including peptide sequences typically referred to as linker sequences or peptide linkers.

"Contiguous" is understood as touching or connected to through an unbroken sequence.

"Detect" refers to identifying the presence, absence or amount of the analyte to be detected.

By "diagnosing" and the like as used herein refers to a clinical or other assessment of the condition of a subject based on observation, testing, or circumstances for identifying a subject having a disease, disorder, or condition based on the presence of at least one indicator, such as a sign or symptom of the disease, disorder, or condition. Typically, diagnosing using the method of the invention includes the observation of the subject for multiple indicators of the disease, disorder, or condition in conjunction with the methods provided herein. A diagnostic methods provide an indicator that a disease is or is not present. A single diagnostic test typically may not provide a definitive conclusion regarding the disease state of the subject being tested.

As used herein, "epitope tag" is understood as a peptide sequence unrelated to the peptide to which it is attached that provides a specific antigen (e.g., myc tag, HAI tag, FLAG tag) or binding site (e.g., GST, 6×His (SEQ ID NO: 14)) for which a commercially available reagent (e.g., monoclonal antibody, affinity matrix) is available to facilitate isolation of a molecule including the epitope tag.

As used herein, the terms "identity" or "percent identity", refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity. The identity between two sequences is a direct function of the number of matching or identical positions. Thus, if a portion of the reference sequence is deleted in a particular peptide, that deleted section is not counted for purposes of calculating sequence identity. Identity is often measured using sequence analysis software e.g., BLASTN or BLASTP (available at www.ncbi.nih.gov/BLAST). Additional, computer programs for determining identity are well-known in the art.

As used herein, "immunoassay" includes any of a number of antibody based assays including LIPS, ELISA, RIA, immunoprecipitation assay, dot blot, slot blot, immunofluorescence, and immunohistochemistry. In certain embodiments, immunoassay does not include western blots.

As used herein, "isolated" or "purified" when used in reference to a polypeptide or, nucleic acid means that a naturally occurring polypeptide or nucleic acid has been removed from its normal physiological environment (e.g., protein isolated from plasma or tissue, optionally bound to another protein) or is synthesized in a non-natural environment (e.g., artificially synthesized in an in vitro transcription or translation system or using chemical synthesis, fragments amplified by PCR and/or generated by restriction digest). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition. An isolated virus or viral vector is a virus that is removed from the cells, typically in culture, in which the virus was produced.

By "agent" is meant any small molecule chemical compound, antibody, nucleic acid molecule, or polypeptide, or fragments thereof.

As used herein, "kits" are understood to contain at least one non-standard laboratory reagent for use in the methods of the invention in appropriate packaging, optionally containing instructions for use. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

As used herein, a "nucleic acid encoding a polypeptide" is understood as any possible nucleic acid that upon (transcription and) translation would result in a polypeptide of the desired sequence. The degeneracy of the nucleic acid code is well understood. Further, it is well-known that various organisms have preferred codon usage, etc. Determination of a nucleic acid sequence to encode any polypeptide is well within the ability of those of skill in the art.

As used herein, "operably linked" is understood as joined, preferably by a covalent linkage, e.g., joining an amino-terminus of one peptide; expressing an enzyme to a carboxy terminus of another peptide; expressing a signal sequence to target the protein to a specific cellular compartment; or joining a promoter sequence with a protein coding sequence, in a manner that the two or more components that are operably linked either retain their original activity, or gain an activity upon joining such that the activity of the operably linked portions can be assayed and have detectable activity, e.g., enzymatic activity or protein expression activity.

As used herein, "plurality" is understood to mean more than one. For example, a plurality refers to at least two, three, four, five, or more.

As used herein, "peptide linker" and the like are understood to be amino acid sequences of essentially any length (e.g., 2, 3, 4, 5, 6, 7, 8, 9, 10, 11, 12, 13, 14, 15, 16, 17, 18, 19, 20, or more amino acids) and are relatively non-antigenic. Peptide linker sequences can be encoded by nucleic acid sequences between nucleic acid sequences encoding functional components of the peptide, e.g., antigenic peptide sequences, reporter peptide sequences, epitope tag sequences, etc. Alternatively, peptide linkers can be short peptide sequences including reactive groups, typically at the termini of the peptide that can be used to join the linker sequences to peptides to allow them to be covalently linked.

A "polypeptide" or "peptide" as used herein is understood as two or more independently selected natural or non-natural amino acids joined by a peptide bond. A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins), shorter amino acids sequences (e.g., fragments of naturally occurring proteins or synthetic polypeptide fragments), or artificial peptide sequences composed of naturally occurring and/or non-naturally occurring peptide sequences.

As used herein, a "reporter protein" or a "reporter polypeptide" is understood as a polypeptide that can be readily detected, preferably quantitatively detected, either directly or indirectly. A reporter polypeptide typically has an enzymatic activity, luciferase activity, alkaline phosphatase activity, beta-galactosidase activity, acetyl transferase activity, or the like, wherein catalysis of a reaction with a substrate by the enzyme results in the production of a product, e.g., light, that can be detected at a specific wavelength of light, radioactivity, or the like, such that the amount of the reporter peptide can be determined in the sample, either as a relative amount, or as an absolute amount by comparison to control samples.

A "sample" as used herein refers to a biological material that is isolated from its environment (e.g., blood or tissue from an animal, cells, or conditioned media from tissue culture) and is suspected of containing, or known to contain an analyte, such as an antibody. A sample can also be a partially purified fraction of a tissue or bodily fluid (e.g., serum or plasma). A reference sample or a control sample can be a sample from a donor not having the disease or condition, including fluid or tissue from a subject. A reference or control sample can also be from an untreated donor or cell culture not treated with an active agent (e.g., no treatment or administration of vehicle only). A reference or control sample can also be taken at a time point prior to contacting the cell or subject with an agent or therapeutic intervention to be tested or at the start of a prospective study.

"Sensitivity and specificity" are statistical measures of the performance of a binary classification test. The sensitivity (also called recall rate in some fields) measures the proportion of actual positives which are correctly identified as such (e.g., the percentage of sick people who are identified as having the condition); and the specificity measures the proportion of negatives which are correctly identified (e.g., the percentage of well people who are identified as not having the condition). They are closely related to the concepts of type I and type II errors. A theoretical, optimal prediction can achieve 100% sensitivity (i.e., predict all people from the sick group as sick) and 100% specificity (i.e., not predict anyone from the healthy group as sick).

The concepts are expressed mathematically as follows:

sensitivity=# true positives/# true positives+# false negatives specificity=# true negatives/# true negatives+# false positives.

A "subject" as used herein refers, to an organism. In certain embodiments, the organism is an animal. In certain embodiments, the subject is a living organism. In certain embodiments, the subject is a cadaver organism. In certain preferred embodiments, the subject is a mammal. In certain embodiments, the subject is a domesticated mammal or a primate including a non-human primate. In certain preferred embodiments, the subject is a mammal that is capable of being infected by a sp. *Borrelia* pathogen. Examples of subjects include humans; monkeys, dogs, cats, mice, rats, cows, horses, goats, and sheep. A human subject may also be referred to as a patient.

A "subject sample" can be a sample obtained from any subject, typically a blood or serum sample, however the method contemplates the use of any body fluid or tissue from a subject. The sample may be obtained, for example, for diagnosis of a specific individual for the presence or absence of sp. *Borrelia* pathogen infection. In certain embodiments, a subject sample can be a sample for screening of a subject tissue (solubilized or treated to release antibodies) or body fluid (e.g., blood, serum, plasma) prior to transplant or transfusion into a recipient.

A subject "suffering from," "suspected of suffering from," or "having" a specific disease, condition, or syndrome has a sufficient number of risk factors or presents with a sufficient number or combination of signs or symptoms of the disease, condition, or syndrome such that a competent individual would diagnose or suspect that the subject has the disease, condition, or syndrome. Methods for identification of subjects suffering from or suspected of suffering from conditions such as sp. *Borrelia* pathogen infection is within the ability of those in the art. Subjects suffering from, and suspected of suffering from, a specific disease, condition, or syndrome are not necessarily two distinct groups.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

As used herein, a "VOVO antigen" is understood as an antigen that includes isolated peptides having sequences of at least one of SEQ ID NO: 4-8 and SEQ ID NO: 9. The peptides can be separate peptides. The peptides can be linked directly by a covalent linkage such as a peptide bond. The peptides can be linked by a peptide linker sequence. Peptide sequences of SEQ ID NO: 4-9 are identical to or significantly identical to portions of the VlsE C6 and OspC peptides of a *Borrelia* sp. bacteria, particularly one of *Borrelia burgdorferi* (Bb), *Bor-*

*relia garinii* (Bg), *Borrelia afzelii* (Ba), and *Borrelia valaisiana*. The VOVO antigens provided herein are based on protein sequences of one of the *Borrelia* sp. However, VOVO antigens can include sequences from more than one *Borrelia* sp. An exemplary *Borrelia burgdorferi* VOVO antigen composition includes at least the peptide sequences amino acids 1-26 of SEQ ID NO: 1 (i.e., SEQ ID NO: 4), a fragment corresponding to the VlsE-Δ1 protein; amino acids 30-40 of SEQ ID NO: 1 (i.e., SEQ ID NO: 5), a fragment corresponding to the OspC protein; and amino acids 41-65 of SEQ ID NO: 1 (i.e., SEQ ID NO: 9), a fragment corresponding to the VlsE-Δ2 protein; and/or a composition that has a peptide sequence that is at least 80%, optionally at least 85% identical, at least 90% identical, or at least 95% identical to SEQ ID NO: 1, wherein a 10-fold molar excess of the peptide or a combination of the peptide sequences, inhibits binding of at least 50% of a peptide comprising the amino acid sequence of SEQ ID NO: 1 to a sample from a subject suffering from an infection by a *Borrelia burgdorferi* pathogen. Competition assays can be performed using any method known in the art, for example, using a BIACORE device.

Similarly, an exemplary *Borrelia garinii* (Bg) VOVO antigen can include isolated peptide sequences SEQ ID NO: 6 and SEQ ID NO: 9; and/or a composition that has a peptide sequence that is at least 80%, optionally at least 85% identical, at least 90% identical, or at least 95% identical to SEQ ID NO: 2, wherein a 10-fold molar excess of the peptide or a combination of the peptide sequences, inhibits binding of at least 50% of a peptide comprising the amino acid sequence of SEQ ID NO: 2 to a sample from a subject suffering from an infection by a *Borrelia garinii* pathogen.

Similarly, an exemplary *Borrelia afzelii* (Ba) VOVO antigen can include isolated peptide sequences SEQ ID NO: 7 or 8 and SEQ ID NO: 9; and/or a composition that has a peptide sequence that is at least 80%, optionally at least 85% identical, at least 90% identical, or at least 95% identical to SEQ ID NO: 3, wherein a 10-fold molar excess of the peptide or a combination of the peptide sequences, inhibits binding of at least 50% of a peptide comprising the amino acid sequence of SEQ ID NO: 3 to a sample from a subject suffering from an infection by a *Borrelia afzelii* pathogen.

A VOVO antigen can also be generated for detection of *Borrelia* sp. infection from any combination of *Borrelia burgdorferi, Borrelia afzelii, Borrelia garinii*, and *Borrelia valaisiana* for the detection of Lyme disease. The VOVO antigen can be a mixed VOVO antigen including a mixture of any combination of peptides having at least 80% sequence identity to each of SEQ ID NO: 1, 2, or 3, wherein a 10-fold molar excess of the peptide inhibits binding of at least 50% of a peptide comprising the corresponding amino acid sequence of SEQ ID NO: 1, 2, or 3 to a sample from a subject suffering from an infection by the corresponding species of *Borrelia*. In certain embodiments, a generic *Borrelia* sp. VOVO antigen can be prepared using a combination of isolated peptide sequences of at least one of SEQ ID NO: 4 or 5; SEQ ID NO: 6; at least one of SEQ ID NO: 7 or 8; and SEQ ID NO: 9, wherein a 10-fold molar excess of the peptide or a combination of the three peptide sequences, inhibits binding of at least 50% of a peptide comprising the amino acid sequence of SEQ ID NO: 1, 2, or 3 to a sample from a subject suffering from an infection by a *Borrelia burgdorferi* (Bb) pathogen, *Borrelia garinii* (Bg) pathogen, or a *Borrelia afzelii* (Ba) pathogen, respectively.

The VOVO antigen can be a mixture of peptides, optionally wherein the peptides are covalently linked to each other (e.g., peptide bond). In certain embodiments, the mixed VOVO antigen is expressed from a single nucleic acid. A mixed VOVO antigen need not be designed for use in the diagnosis of all *Borrelia* sp. infections. In certain embodiments, the mixed VOVO antigen can be an antigen for detection of both *Borrelia* sp. present in Eurasia (*Borrelia afzelii* and *Borrelia garinii*). A subject will typically know if a potential Lyme infection was picked up in the US or Eurasia. However, a single test to detect antibodies to any of the species of *Borrelia* known to cause Lyme disease could allow for the use of a single test internationally.

The fragments corresponding to each of the VlsE and OspC peptides can be mixed together and used in an immunoassay. When the peptides are expressed separately, preferred assay methods include those in which the antigen is bound to a solid surface prior to contacting the antigen with a serum sample (e.g., ELISA assay). The combination of the sequences in close proximity to each other allows for the binding of the polyclonal antibodies produced in an immune response to bind to more than one site on the surface on which the antigens are coated, increasing the apparent affinity of the antibodies. When binding of the antigens to the antibodies present in serum is performed in solution (e.g., in an immunoprecipitation assay such as a LIPS assay), it is preferred that the peptide sequences are covalently linked to each other. A peptide including all of the fragments can be easily produced using an expression construct in which the three sequences corresponding to a fragment of each of the VlsE-Δ1, VlsE-Δ2, and OspC from the desired *Borrelia* sp. joined in frame, optionally by linker sequences, and operably linked to a promoter sequence appropriate for the system in which the protein is to be expressed. Although the VOVO peptide exemplified in the instant application, includes domains in the following order: VlsE-Δ1, OspC, VlsE-Δ2, and OspC, it is understood that any combination or order of the fragments of the protein sequences is possible, e.g., VlsE-Δ1-VlsE-Δ21-OspC; VlsE-Δ1-OspC-VlsE-Δ2; OspC-VlsE-Δ1-VlsE-Δ2; VlsE-Δ2-VlsE-Δ1-OspC; VlsE-Δ2-OspC-VlsE-Δ1; OspC-VlsE-Δ2-VlsE-Δ1; etc. Analogous combinations can be made based on the sequences SEQ ID NO: 6 and 9. Analogous combinations can be made based on the sequences SEQ ID NO: 7, 8, and 9. It is understood that more than three fragments can be joined together (e.g., 4, 5, 6, 7, 8, 9, 10, etc.), e.g., to facilitate expression of the peptide sequences, provide desired stoichiometry and/or relative positions of the fragments, etc. It is understood that VlsE-Δ1, VslE Δ2, and OspC fragments from different *Borrelia* sp. can be mixed or joined together. It is further understood that VOVO antigens can be linked to other protein sequences, e.g., reporter constructs, epitope tags, etc.

In an alternative embodiment, the "V" and/or "O" fragments can be expressed with an epitope tag, e.g., a 6×His tag (SEQ ID NO:14), and coated onto a bead for binding to antibodies present in sera.

In an alternative embodiment, the "V" and/or "O" fragments can be joined using any of a number of commercially available cross-linking reagents. The fragments can be joined in any order or any orientation as long as the linking agents do not disrupt binding of the antibodies to the antigen.

Other methods for joining the "V" and/or "O" fragments are well-known to those of skill in the art.

Ranges provided herein are understood to be shorthand for all of the values within the range. This includes all individual sequences when a range of SEQ ID NOs is provided. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION OF THE INVENTION

Currently, there is a need for sensitive and specific testing to identify and monitor Lyme-infected individuals. A variety of immunoassays, including immunofluorescence assays, Western blot, and ELISAs have been employed to detect antibodies to Bb proteins. One of the most useful approaches employs defined short peptides derived from VslE and OspC for testing (Bacon, et al., 2003. *J Infect Dis* 187:1187-99; Embers, et al., 2007. *Clin Vaccine Immunol* 14:931-6.; Liang, et al., 1999. *J Immunol* 163:5566-73; and Liang, et al., 1999. *J Clin Microbiol* 37:3990-6). For example, the most sensitive ELISA using the C6 peptide of VslE, matches the 2-tiered Western blotting in sensitivity and specificity. While there is an interest in using the C6 ELISA and other serological tests for monitoring antibiotic therapy of Lyme infected patients, these studies are hampered by the limited dynamic range of these solid phase immunoassays and the need for time consuming and cumbersome serum dilutions to obtain values in the linear range (Fleming, et al., 2004. *Eur J Clin Microbiol Infect Dis* 23:615-8; Levy, et al., 2008. *Clin Vaccine Immunol* 15:115-9; Philipp, et al., 2003. *J Clin Microbiol* 41:4955-60; and Philipp, et al., 2005. *Clin Diagn Lab Immunol* 12:1069-74).

The serological laboratory tests most widely available and employed are the Western blot and ELISA. A two-tiered protocol is recommended by the CDC: the sensitive ELISA test is performed first, and if it is positive or equivocal then the more specific Western blot is run (Wilske et al. 2005. *Ann. Med.* 37: 568-79). However, Western blots are cumbersome, rarely used in clinical laboratories making the tests more inconvenient, and are not adaptable to high throughput methods. The reliability of testing in diagnosis remains controversial, however, studies show that the IgM Western blot has a specificity of 94-96% for patients with clinical symptoms of early Lyme disease. The initial ELISA test has a sensitivity of about 70%, and in two tiered testing, the overall sensitivity is only 64% although this rises to 100% in a subset of people with disseminated symptoms, such as arthritis.

Luciferase Immunoprecipitation System (LIPS) is a highly sensitive immunoprecipitation technology that utilizes mammalian cell-produced, recombinant fusion protein antigens for efficiently evaluating antibody responses (see US Patent Publication 2007/0259336 and Burbelo et al. 2005. *BMC Biotechnol.* 5:22, which are hereby incorporated by reference). LIPS shows strong diagnostic performance for detecting antibodies to infectious agents (e.g., HCV, HIV, HTLV-I, and filarial infectious agents) and provides new tools to monitor drug treatment and sub-stratify disease states. LIPS is highly useful for profiling autoimmunity and in one study showed several advantages over a highly sensitive radioactive in vitro transcription/translation assay for detecting anti-IA2 autoantibodies associated with type I diabetes.

LIPS is based on fusing protein antigens to a light emitting enzyme reporter, *Renilla* luciferase (Ruc), and then using these antigens in immunoprecipitation assays with sera samples and Protein A/G beads. Following washing, light production is measured yielding highly quantitative antibody titers. While LIPS has already shown high sensitivity for detecting fungal, helminthic, filarial, and a variety of viral infection agents, its utility to accurately evaluate humoral responses to bacterial pathogen antigens has not been assessed. As described below, LIPS was used to evaluate antibody responses to a panel of Bb antigens for the serological diagnosis of Lyme disease. Following the evaluation of the training set, several antigens including VslE, DbpA, DbpB, BMP, and FlaB, showed high performance. Nevertheless, the antigen with the greatest dynamic range of detection and highest sensitivity and specificity was composed of a synthetic gene (designated VOVO) containing 2 alternating copies of immunoreactive peptides derived from VslE and OspC antigens. Analysis of an independent validation serum set with VOVO showed 94% sensitivity and 100% specificity, and markedly out-performed the C6 ELISA. Without serum dilution, LIPS also showed a wide dynamic range of detection making it a practical tool for accurately quantifying anti-Lyme antibodies. These results demonstrate that an immunoassay based on the VOVO antigen, preferably LIPS screening with VOVO antigen, optionally with other *Borrelia* sp. proteins (e.g., VslE-Δ1 (Accession No: GU182319), VslE-Δ2 (Accession No: GU182320); Fla (GenBank AAC66541); Bmp (GenBank NP_212517); Dbp (GenBank AAC70025), DBpA (GenBank YP_002455347), OspC2-Δ1 (GenBank NP_047005)) or fragments therefrom, is an efficient high-throughput method for accurately determining anti-Lyme patient antibody responses, including without serum dilution.

The test can be used as part of a routine screening panel for sp. *Borrelia* pathogen progression or regression in a subject by detecting binding of antibodies to VOVO antigens.

Further, the method can be used for monitoring donated blood, organs, and/or tissues for the presence of sp. *Borrelia* pathogen infection.

EXAMPLES

It should be appreciated that the invention should not be construed to be limited to the examples that are now described; rather, the invention should be construed to include any and all applications provided herein and all equivalent variations within the skill of the ordinary artisan.

Example 1

Material and Methods

Patient Sera. Serum was obtained from patients or volunteers under institutional review board approved protocols at the Clinical Center, National Institute of Allergy and Infectious Diseases, NIH. The initial training set (n=46) included serum from 11 EM, 8 multiple erythema migrans (MEM), 2 Lyme palsy, 6 Lyme arthritis, 1 late Lyme neuroborreliosis, 10 post-Lyme disease syndrome (PLDS) subject samples, and 8 uninfected control sera subject samples were analyzed. Testing of the validation set consisted of 225 coded serum samples. This validation cohort consisted of 59 control sera and 141 samples from patients with established Lyme disease. The codes for the validation cohort was broken only after titers were established and categorization of Lyme infection status had been made. The antibody titer results for the validation cohort obtained by LIPS was also compared with the C6 ELISA. Of note, an additional 40 samples with uncertain diagnosis for Lyme disease were also analyzed by LIPS and the C6 ELISA, but were not used in calculation of sensitivity and specificity.

Figure 3:
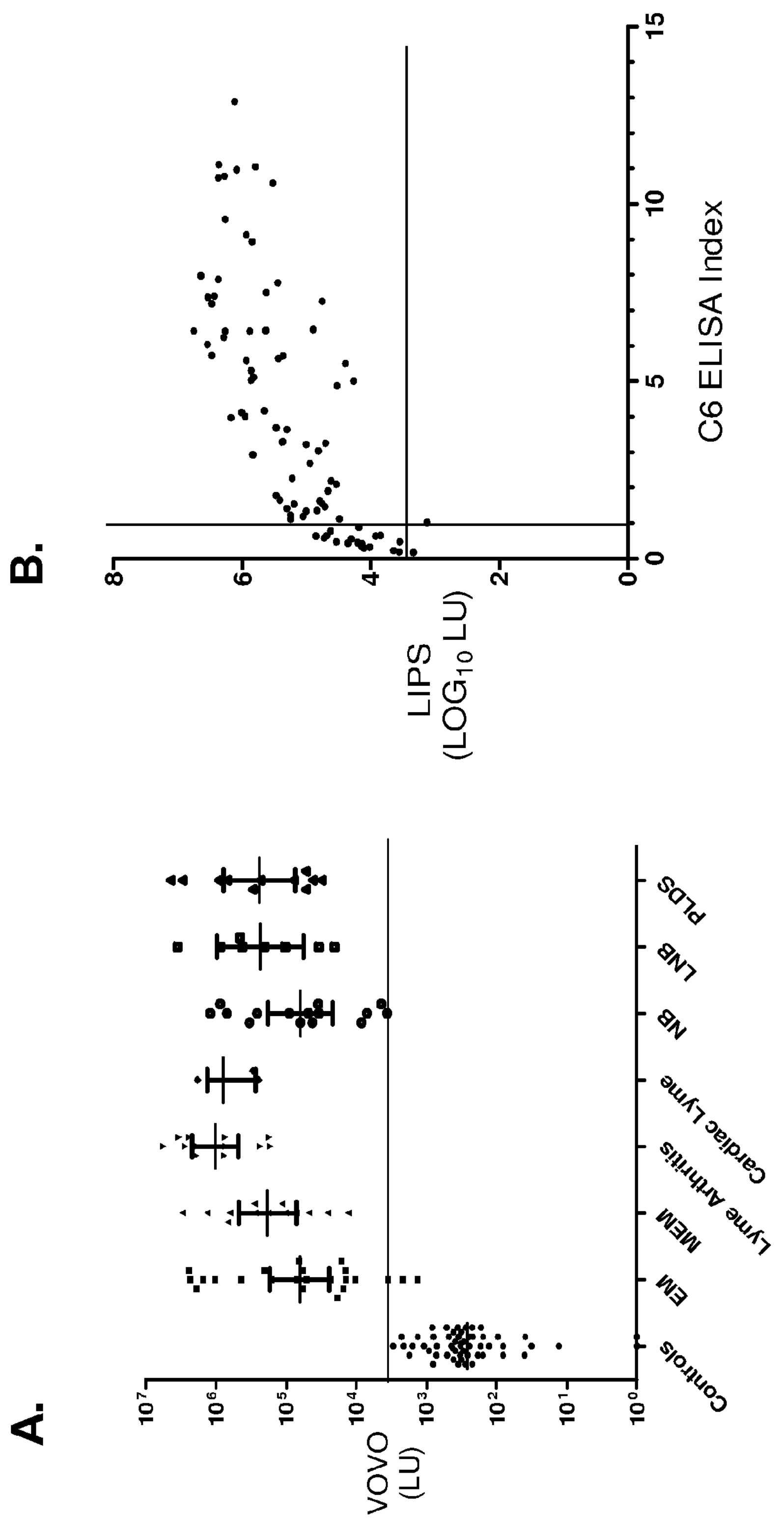
FIGS. 3A-3B show that the VOVO antigen has 94% sensitivity and 100% specificity.
Figure 5:
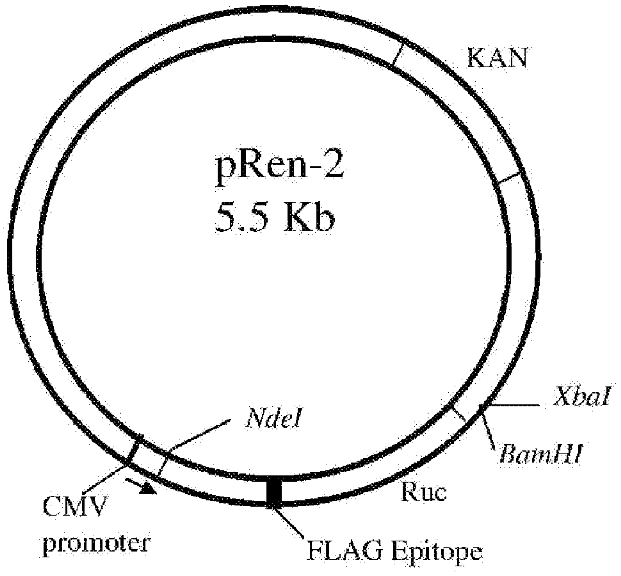
FIG. 5 is a schematic of the pREN2 mammalian expression vector. Features indicated are CMV (cytomegalovirus) promoter, the N-terminal FLAG epitope and Ruc. Sequences for Ruc are in bold. cDNAs for tumor antigens were cloned downstream of Ruc between the BamHI-XhoI sites. Sequences of the FLAG-epitope operably linked to luciferase (SEQ ID NO: 10 and 11) and the multiple cloning site (SEQ ID NO: 12 and 13) are provided. (Plasmid is described in Burbelo et al., 2005. *BMC Biotechnology.* 5:22, which is hereby incorporated by reference).

Generation of Ruc-Antigen Fusion Constructs. pREN2, a mammalian *Renilla* luciferase (Ruc) expression vector, was used to generate all plasmids (FIG. 3). Bb genes were amplified by PCR specific linker-primer adapters using synthetic cDNA templates assembled in the investigators laboratory or obtained from Blue Heron Biotechnology (Seattle, Wash.). Gene-specific primers were then used in PCR amplifications for generating cDNA sequences for cloning as C-terminal fusions of Ruc. For each C-terminal fusion, a stop codon was included at the end of the coding sequence. The nucleotide and protein sequence for VOVO has GenBank Accession number GU134803. The peptide encoded by VOVO is MKKDDQIAAAIALRGMAKDGKFAVKELTSPVVA ESPKKP MKKDDQIAAAMVLRGMAKDGOQFALKPVVAESPKKP (SEQ ID NO: 15), in which the peptide sequence from VslE is underlined and the peptide sequence from OspC is in italics. Two constructs, VslE-Δ1 and VslE-Δ2, containing the VslE peptide sequences have GenBank Accession sequences GU182319 and GU182320 were also tested. DNA sequencing was used to confirm the integrity of all the DNA constructs. Plasmid DNA was then prepared from the different pREN2 expression vectors using a Qiagen Midi preparation kit.

LIPS Analysis. Following transfection of mammalian expression vectors, crude protein extracts were obtained as described in Burbelo, et al. 2008. *Biochem Biophys Res Commun* 366:1-7, which is hereby incorporated by reference.). A detailed protocol of the LIPS assay is now available along with a corresponding technical video from the Journal of Visualized Experiments (Burbelo et al., 2009, *J. Vis. Exp.* www.jove.com/index/Details.stp?ID=1549).

Data Analysis. The GraphPad Prism software (San Diego, Calif.) was used for statistical analysis. Results for qualitative antibody titers between the controls and Bb-infected individuals are reported as the mean+5 standard deviation (SD). Mann-Whitney U tests were used to compare the antibody titers among the groups.

Example 2

LIPS Detection of Antibody Responses to a Panel of Bb Antigens

Previous studies from various laboratories have identified a large number of Bb antigens useful for serological screening of Lyme disease. Fifteen different Bb antigens including FlaB, BMP, Dbp-A, DbpB, OspC, OspA, Bbk and 2 different VlsE constructs were initially synthetically assembled and constructed as C-terminal fusion with Ruc. LIPS evaluation of these different antigens began by testing a small cohort of serum samples (n=44) consisting of serum from 11 EM, 8 MEM, 2 Lyme palsy, 6 Lyme arthritis, 1 late Lyme neuroborreliosis, 10 PLDS subjects, and 8 uninfected control subject serum samples. To easily visualize the differing immunoreactivity to this large antigen panel, we employed our previously described heat map analysis to graphically display the antibody responses using a login scale to the most informative antigens (FIG. 1A). From these tests, 6 of these Bb proteins showed weak or non-existent antibody signals (BBk, OspA, OspF, Crasp, OspC, DbpA (with signal peptide), while 7 others (VlsE-Δ1, VlsE-Δ2; Fla; Bmp; DbpA without signal peptide, DbpB without signal peptide, OspC2-Δ1 without signal peptide) showed high levels of immunoreactivity with over 50% of the Lyme samples (FIG. 1A). Based on the mean plus 5 standard deviations, the most informative antigen in the initial panel was VlsE-Δ1 and was followed by VslE-Δ2. Other antigens such as DbpA and Dbp-B showed nearly identical serological activity but were less sensitive.

Next, a new synthetic antigen was generated and tested. This new antigen was synthetically assembled in one recombinant protein. The new antigen was designated VOVO and contained 2 alternating copies of immunoreactive peptides derived from VslE and OspC antigens. The rational behind VOVO's design was that the repeated antigenic peptides from the 2 different proteins might increase the valency, and thereby apparent affinity, and capture low affinity antibodies. From LIPS testing, VOVO appeared to be an effective antigen. Without wishing to be bound by mechanism, it is suggested that the use of the fragments provided herein allows for the unmasking of hidden or cryptic immunodominant antigen sequences to allow for binding of serum antibodies. The mean anti-VOVO antibody titer in the 38 Lyme samples was 1,716, 000 LU and was over 1000-fold higher than antibody titer of 1,395 LU in the controls (Mann Whitney U test, $P<0.0017$). Using a cut-off derived from the mean plus 3 SD of the controls, 84% of the Lyme samples were VOVO positive and all the sera from uninfected controls were negative (FIG. 1B), Only a few serum samples including 1 PLDS and 4 EM samples were seronegative for anti-VOVO antibodies, which were also negative by C6 ELISA. These promising results indicate that VOVO is a highly useful antigen for LIPS screening of Lyme sera, including in the early stage after infection, e.g., within 1-2 weeks of infection.

Example 3

Using VOVO with a New Independent Validation Cohort

Figure 2:
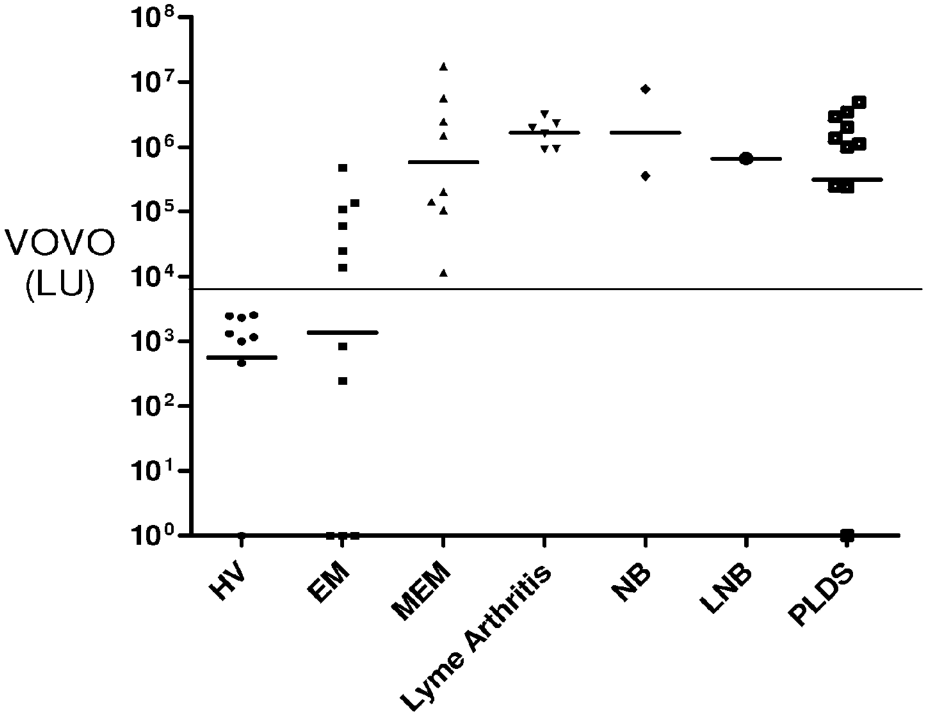
FIG. 2 includes a scatter plot of the antibody responses from the LIPS VOVO test. Shown are results from 11 EM, 8 multiple erythema migrans (MEM), 2 Lyme palsy, 6 Lyme arthritis, 1 late Lyme neuroborreliosis, post-Lyme disease syndrome (PLDS) patient samples and 8 uninfected control samples. Each symbol represents a serum sample from an individual patient. The geometric mean is shown as the bar.

To test the effectiveness of VOVO and compare it with the C6 ELISA, a new validation cohort of 225 blinded sera were evaluated. Following breaking the code, the LIPS antibody titer data were analyzed. Similar to the training set, the mean anti-VOVO antibody titer in the 141 Lyme samples was 589, 200 LU and was markedly higher than antibody titer of 537 LU in the 59 controls (Mann Whitney U test, $P<0.0017$). In order to determine the sensitivity and specificity, a diagnostic cut-off 5 value of LU based on the mean plus 5 SD of the control samples was used. Using this cut-off, the VOVO LIPS test showed 94% sensitivity and 100% specificity with these samples (FIG. 2A). The C6 ELISA had a markedly lower diagnostic performance of 76% sensitivity and 98% specificity. ROC analysis showed that the area under the curves for antibodies to LIPS and C6 ELISA were statistically different ($p=0.005$). The VOVO LIPS tests also had a markedly greater dynamic range of detection (FIG. 2A) and did not require dilution. However, as shown in FIG. 2B, correlation of $\log^{10}$ transformed LIPS values with the C6 ELISA values showed that both assays tracked each other ($rs=0.82$, $p<0.00001$).

Example 4

Generation of a VOVO Antigen for Detection of Antibodies to Other *Borrelia* sp Based on the analysis performed for antigens of Bb, antigens were selected based on homology with the VslE sequences selected above from other *Borrelia* sp. Alignments of the Bb VslE-Δ1 and VslE-Δ2 antigen sequences against sequences from VslE proteins from one *B. garinii* and two *B. afzelii* sequences are shown in FIG. 4B. The OspC fragment sequence in the Bb VOVO antigen has the same sequence as is found in *B. garinii* and two *B. afzelii*. As such, these sequence alignments indicate that *B. garinii* and *B. afzelii* can be useful in the context of a VOVO antigen for detection of infection with a pathogen from those species.

Upon generation of VOVO antigens for *B. garinii* and *B. afzelii*, the antigens are validated using the method provided in the example above. A set of samples from subjects known to have been infected with either *B. garinii* or *B. afzelii* are analyzed for binding to the VOVO antigen. The samples are then unblinded the sensitivity and specificity of the test are analyzed. In addition, an assay to detect infection by *B. garinii* or *B. afzelii* using the VOVO antigen containing Bb sequences can be tested to determine if there is sufficient cross-reactivity to allow the antigens to be used cross-species.

Alternatively, other proteins from *B. garinii* and *B. afzelii* are tested for their utility as diagnostic antigens. For example, full length proteins and fragments of *B. garinii* and *B. afzelii* proteins FlaB, BMP, Dbp-A, DbpB, OspC, OspA, Bbk, and VslE are tested for their utility as antigens for detection of infection with *B. garinii* or *B. afzelii.*

All references, patents, patent applications, and GenBank numbers as of the date of filing of the instant application are hereby incorporated by reference as if they were each incorporated individually.

*Borrelia afzelii* - OspC
MKKNTLTAILMTLFLFISCNNSGKVGILTSTNPADESAKGPNLTEISKKITDSNAFVLAVKEVETLVLSIDELAK

KAIGQKIDNNNGLAALNNQNGSLLAGAYAISTLITEKLSKLKNLEELKTEIAKAKKCSEEFTNKLKSGHADLGKQ

DATDDHAKAAILKTHATTDKGAKEFKDLFESVEGLLKAAQVALTNSVKELTSPVVAESPKKP* (SEQ ID NO: 16)

*Borrelia burgdorferi* - OspC
MKKNTLSAILMTLFLFISCNNSGKDGNTSANSADESVKGPNLTEISKKITDSNAVLLAVLEVEALLSSIDEIAAK

AIGKKIHQNNGLDTENNHNGSLLAGAYAISTLIKQKLDGLKNEGLKEKIDAAKKCSETFTNKLKEKHTDLGKEGV

TDADAKEAILKTNGTKTKGAEELGKLFESVEVLSKAAKEMLANSVKELTSPVVAESPKKP* (SEQ ID NO: 17)

*Borrelia garinii* - OspC
mkkntlsail mtlflfiscn nsggdtastn pdesakgpnl tviskkitds nafvlavkev ealissidel ankaigkvih qnnglnanag qngsllagay aistlitekl sklknseeln kkieeaknhs eaftnrlkgs haqlgvaaat ddhakeailk snptkdkgak elkdlsesve slakaacqeal ansvkeltnp vvaespkkp (SEQ ID NO: 18)

FlaB (flagellin; p41)
Amino acids 20-336 of B.B. B31 strain (GenBank AAC66541)
20 anlsktqekl ssgyrinras ddaagmgvsg kinaqirgls 61 qasrntskai nfiqttegnl nevekvlvrm kelavqsgng tysdadrgsi qieieqltde 121 inriadqaqy nqmhmlsnks asqnvrtaee lgmqpakint paslsgsqas wtlrvhvgan 181 qdeaiavniy aanvanlfsg egaqtaqaap vqegvqqega qqpapataps qggvnspvnv 241 tttvdantsl akienairmi sdqranlgaf qnrlesikns teyaienlka syaqikdatm 301 tdevvaattn siltqsamam iaqanqvpqy vlsllr*336 (SEQ ID NO: 19)

BmpA
Amino acids 26-339 of B.b. B31 strain (GenBank NP_212517 )
26 seipk vsliidgtfd dksfnesaln gvkkvkeefk 61 ielvlkesss nsylsdlegl kdagsdliwl igyrfsdvak vaalqnpdmk yaiidpiysn 121 dpipanlvgm tfraqegafl tgyiaaklsk tgkigflggi egeivdafry gyeagakyan 181 kdikistqyi gsfadleagr svatrmysde idiihhaagl ggigaievak elgsghyiig 241 vdedqaylap dnvitsttkd vgralnifts nhlktntfeg gklinyglke gvvgfvrnpk 301 misfelekei dnlsskiink eiivpsnkes yekflkefi*339 (SEQ ID NO: 20)

DbpB amino 25-280 of B.b. sensu lato (GenBank AAC70025)
25 alesss kdlknkilki kkdatgkgvl feaftglktg 61 skvtsgglal reakvqaive tgkflkiiee ealklketgn sgqflamfdl mlevvesled 121 vgiiglkarv leesknnpin taerllaaka qienqlkvvk ekqniengge kknnkskkkk*
(SEQ ID NO: 21)

-continued

```
DbpA amino 33-194 of B.b. of Zs7 strain (GenBank YP_002455347)
                                    33 etkiiler sakdiidein kikkdaadnn

 61 vnfaafkedk tgskvsensf ileakmrgtt vaekfvtaie geatklkktg ssgefsamyn

121 mmlevsgple elgvlrmtkt vtdaaeqhpt ttaegileia ktmktklqrv htknycalkk

181 kenpsftdek cknn*194 (SEQ ID NO: 22)

OspC amino acids 22-210 of B.b. B31 strain (GenBank NP_047005)
                        22 sgkdgntsa nsadesvkgp nlteiskkit dsnavllavk

 61 eveallssid eiaakaigkk ihqnngldte nnhngsllag ayaistlikq kldglknegl

121 kekidaakkc setftnklke khtdlgkegv tdadakeail ktngtktkga eelgklfesv

181 evlskaakem lansvkelts pvvaespkkp*210 (SEQ ID NO: 23)

LOCUS GU182319 171 bp DNA linear SYN 09-FEB-2010
DEFINITION      Synthetic construct immunodominant VlsE protein (Vs1E-d1) gene,
                partial cds.

ACCESSION       GU182319

VERSION         GU182319.1 GI: 288189225

translation = "ADAAEQDGKKPEEAKNPIAAAIGDKDGDAEFNQDDMKKDDQIAA

                       AIALRGMAKDGK" (SEQ ID NO: 24)

ORIGIN
  1 gccgacgccg ccgagcagga cggcaagaag cccgaggagg ccaagaaccc catcgccgcc

 61 gccatcggcg acaaggacgg cgacgccgag ttcaaccagg acgacatgaa gaaggacgac

121 cagatcgccg ccgccatcgc cctgcgcggc atggctaagg atggaaagtg a (SEQ ID NO: 25)

LOCUS GU182320 483 bp DNA linear SYN 09-FEB-2010
DEFINITION      Synthetic construct immunodominant VlsE protein (Vlse-d2) gene,
                partial cds.

ACCESSION       GU182320

translation = GAGKLFGKAGAAAHGDSEAASKAAGAVSAVSGEQILSAIVTAAD

AAEQDGKKPEEAKNPIAAAIGDKDGGAEFGQDEMKKDDQIAAAIALRGMAKDGKFAVK

DGEKEKAEGAIKGAAESAVRKVLGAITGLIGDAVSSGLRKVGDSVKAASKETPPALNK" (SEQ ID NO: 26)

ORIGIN
  1 ggtgccggta agttgttcgg taaggctggt gccgcagcac acggtgatag tgaagccgcc

 61 tccaaggctg ccggtgctgt aagcgctgtc tccggtgaac aaatcttgtc cgctatagtt

121 accgctgccg atgcagctga acaagatggt aaaaagccag aagaagcaaa gaatcccatt

181 gctgctgcaa ttggtgataa ggatggtggt gccgaatttg gtcaagatga aatgaaaaag

241 gatgatcaaa tcgcagccgc catcgccctt cgcggtatgg ccaaagatgg taaatttgca

301 gttaaggatg gtgaaaaaga aaaagctgaa ggcgcaatta agggtgccgc tgaaagcgcc

361 gtacgcaagg tactcggtgc aattacgggt ctcattggtg atgcagtgag ctcaggtctg

421 cgcaaggtgg gtgatagtgt gaaagctgcc agcaaagaaa caccccccgc cctcaacaag

481 tag (SEQ ID NO: 27)

LOCUS ADA82861 192 aa linear BCT 27-JAN-2010
DEFINITION      VlsE [Borrelia burgdorferi].

ACCESSION       ADA82861

VERSION         ADA82861.1 GI:282555520

DBSOURCE        accession GQ506415.1

KEYWORDS        .

SOURCE          Borrelia burgdorferi (Lyme disease spirochete)
```

-continued

```
  1 egaikevsel ldklvkavkt aegassgtaa igevvadada akvadkasvk giakgikeiv

 61 eaaggseklk avaaakgenn kgagklfgka gaaahagdse aaskaagavs avsgeqilsa

121 ivtaadaaeq egkkpaeakn piaaaignkd ggaefgqdem kkddqiaaai alrgmakdgk

181 favkednkkg ka (SEQ ID NO: 28)

  1 gagggggcta ttaaggaagt tagcgagttg ttggataagc tggtaaaagc tgtaaagaca

 61 gctgaggggg cttcaagtgg tactgctgca attggagaag ttgtggctga tgctgatgct

121 gcaaaggttg ctgataaggc gagtgtgaag ggattgcta aggggataaa ggagattgtt

181 gaagctgctg gggggagtga aaagctgaaa gctgttgctg ctgctaaagg ggagaataat

241 aaaggggcag ggaagttgtt tgggaaggct ggtgctgctg ctcatgctgg ggacagtgag

301 gctgctagca aggcggctgg tgctgttagt gctgttagtg gggagcagat attaagtgcg

361 attgttacgg ctgctgatgc ggctgagcag gagggaaaga agcctgcaga ggctaaaaat

421 ccgattgctg ctgctattgg gaataaagat gggggtgcgg agtttggtCa ggatgagatg

481 aagaaggatg atcagattgc tgctgctatt gctttgaggg ggatggctaa ggatggaaag

541 tttgctgtga aggaggataa taagaaaggg aaggct (SEQ ID NO: 29)
```

```
LOCUS AAN87831 174 aa linear BCT 07-APR-2003
DEFINITION       vls recombination cassette Vls7 [Borrelia garinii].

ACCESSION        AAN87831

VERSION          AAN87831.1 GI:29075690

DBSOURCE         accession AY100633.1

SOURCE           Borrelia garinii

ORIGIN

  1 asaatgnaai gdvvngdvak akggdaasvn giakgikgiv daaekadake gklnaagaeg

 61 ttnadagklf vknagnvgge agdagkaaaa vaavsgeqil kaivdaakdg gekqgkkaad

121 atnpidaaig gtndndaaaa fatmkkddqi aaamvlrgma kdgqfalkda aaah
(SEQ ID NO: 30)

ORIGIN

  1 gcaagtgctg ctactggtaa tgcagcgatt ggagatgttg ttaatggtga tgtggcaaaa

 61 gcaaaaggtg gtgatgcggc gagtgttaat gggattgcta aggggataaa ggggattgtt

121 gatgctgctg agaaggctga tgcgaaggaa gggaagttga atgctgctgg tgctgagggt

181 acgactaacg cggatgctgg gaagttgttt gtgaagaatg ctggtaatgt gggtggtgaa

241 gcaggtgatg ctgggaaggc tgctgctgcg gttgctgctg ttagtgggga gcagatatta

301 aaagcgattg ttgatgctgc taaggatggt ggtgagaagc agggtaagaa ggctgcggat

361 gctacaaatc cgattgacgc ggctattggg ggtacaaatg ataatgatgc tgctgcggcg

421 tttgctacta tgaagaagga tgatcagatt gctgctgcta tggttctgag ggga atggct

481 aaggatgggc aatttgcttt gaaggatgct gctgctgctc at (SEQ ID NO: 31)

LOCUS AY100628 606 bp DNA linear BCT 18-MAR-2003
DEFINITION       Borrelia afzelii strain ACAI vls recombination silent cassette
                 locus, complete sequence.

ACCESSION        AY100628 REGION: 1..606

translation = "ESAVDGVSKWLEEMIKAAKEAATKGGTGGGSEKIGDVGAANNQG

AVADKDSVKGIAKGIKGIVDAAGKAFGKDGNALTGVKEVADEAGANEDAGKLFAGNAG

NAAAADIAKAAGAVTAVSGEQILKAIVDGAGGAAQDGKKAAEAKNPIAAAIGADAAGA

                    DFGDDMKKSDKIAAAIVLRGVAKSGKFAVANAAKKESVKSAV" (SEQ ID NO: 32)
```

-continued

```
ORIGIN
  1 gagagtgctg ttgatggggt tagcaagtgg ttagaagaga tgataaaagc tgctaaggag

 61 gctgctacaa agggtggtac tggtggtggt agcgaaaaga ttggggatgt tggtgctgct

121 aataatcagg gtgctgtagc tgataaggac agtgttaagg ggattgcgaa ggggataaag

181 gggattgttg atgctgctgg gaaggctttt ggtaaggatg gtaatgcgct gacaggtgta

241 aaagaagttg ctgatgaggc tggggctaac gaggatgcgg ggaagttgtt tgctggtaat

301 gctggtaatg ctgctgctgc tgacattgcg aaggcggctg gtgctgttac tgcggttagt

361 ggggagcaga tactgaaagc tattgttgat ggtgctggtg gtgcggctca agatggtaaa

421 aaggctgcgg aggctaagaa tccgattgca gctgcgattg ggctgatgc tgctggtgcg

481 gattttggtg atgatatgaa gaagagtgat aagattgctg cggctattgt tttgaggggg

541 gtggctaaga gtggaaagtt tgctgttgct aatgctgcta agaaggagag tgtgaagagt

601 gctgtg (SEQ ID NO: 33)
```

We claim:

1. A composition comprising an isolated peptide, wherein said isolated peptide comprises SEQ ID NO: 1.

2. The composition of claim 1, wherein the isolated peptide consists of SEQ ID NO: 1.

3. The composition of claim 1, wherein the composition further comprises a reporter polypeptide covalently linked to the isolated peptide.

4. A kit comprising the isolated peptide of claim 1.

5. A composition comprising an isolated nucleic acid encoding the isolated peptide of claim 1.

6. A kit comprising the nucleic acid of claim 5 in appropriate packaging.

* * * * *

SEQUENCE LISTING

```
<160> NUMBER OF SEQ ID NOS: 33

<210> SEQ ID NO 1
<211> LENGTH: 74
<212> TYPE: PRT
<213> ORGANISM: Borrelia burgdorferi

<400> SEQUENCE: 1

Met Lys Lys Asp Asp Gln Ile Ala Ala Ala Ile Ala Leu Arg Gly Met
1               5                   10                  15

Ala Lys Asp Gly Lys Phe Ala Val Lys Glu Leu Thr Ser Pro Val Val
            20                  25                  30

Ala Glu Ser Pro Lys Lys Pro Met Lys Lys Asp Asp Gln Ile Ala Ala
        35                  40                  45

Ala Met Val Leu Arg Gly Met Ala Lys Asp Gly Gln Phe Ala Leu Lys
    50                  55                  60

Pro Val Val Ala Glu Ser Pro Lys Lys Pro
65                  70


<210> SEQ ID NO 2
<211> LENGTH: 72
<212> TYPE: PRT
<213> ORGANISM: Borrelia garinii

<400> SEQUENCE: 2

Cys Met Lys Lys Asp Asp Gln Ile Ala Ala Ala Met Val Leu Arg Gly
1               5                   10                  15

Met Ala Lys Asp Gly Gln Phe Ala Leu Lys Pro Val Val Ala Glu Ser
            20                  25                  30

Pro Lys Lys Pro Cys Met Lys Lys Asp Asp Gln Ile Ala Ala Ala Met
        35                  40                  45

Val Leu Arg Gly Met Ala Lys Asp Gly Gln Phe Ala Leu Lys Pro Val
    50                  55                  60

Val Ala Glu Ser Pro Lys Lys Pro
65                  70


<210> SEQ ID NO 3
<211> LENGTH: 73
<212> TYPE: PRT
```

-continued

<213> ORGANISM: Borrelia afzelii

<400> SEQUENCE: 3

```
Cys Met Lys Lys Ser Asp Lys Ile Ala Ala Ala Ile Val Leu Arg Gly
1               5                   10                  15

Val Ala Lys Ser Gly Lys Phe Ala Val Ala Pro Val Val Ala Glu Ser
            20                  25                  30

Pro Lys Lys Pro Cys Met Lys Lys Arg Asn Asp Lys Ile Val Ala Ala
        35                  40                  45

Ile Val Leu Arg Gly Val Ala Lys Asp Gly Lys Phe Ala Ala Ala Pro
    50                  55                  60

Val Val Ala Glu Ser Pro Lys Lys Pro
65                  70
```

<210> SEQ ID NO 4
<211> LENGTH: 26
<212> TYPE: PRT
<213> ORGANISM: Borrelia burgdorferi

<400> SEQUENCE: 4

```
Met Lys Lys Asp Asp Gln Ile Ala Ala Ala Ile Ala Leu Arg Gly Met
1               5                   10                  15

Ala Lys Asp Gly Lys Phe Ala Val Lys Glu
            20                  25
```

<210> SEQ ID NO 5
<211> LENGTH: 25
<212> TYPE: PRT
<213> ORGANISM: Borrelia burgdorferi

<400> SEQUENCE: 5

```
Met Lys Lys Asp Asp Gln Ile Ala Ala Ala Met Val Leu Arg Gly Met
1               5                   10                  15

Ala Lys Asp Gly Gln Phe Ala Leu Lys
            20                  25
```

<210> SEQ ID NO 6
<211> LENGTH: 26
<212> TYPE: PRT
<213> ORGANISM: Borrelia garinii

<400> SEQUENCE: 6

```
Cys Met Lys Lys Asp Asp Gln Ile Ala Ala Ala Met Val Leu Arg Gly
1               5                   10                  15

Met Ala Lys Asp Gly Gln Phe Ala Leu Lys
            20                  25
```

<210> SEQ ID NO 7
<211> LENGTH: 26
<212> TYPE: PRT
<213> ORGANISM: Borrelia afzelii

<400> SEQUENCE: 7

```
Cys Met Lys Lys Ser Asp Lys Ile Ala Ala Ala Ile Val Leu Arg Gly
1               5                   10                  15

Val Ala Lys Ser Gly Lys Phe Ala Val Ala
            20                  25
```

<210> SEQ ID NO 8
<211> LENGTH: 27
<212> TYPE: PRT

```
<213> ORGANISM: Borrelia afzelii

<400> SEQUENCE: 8

Cys Met Lys Lys Arg Asn Asp Lys Ile Val Ala Ala Ile Val Leu Arg
1               5                   10                  15

Gly Val Ala Lys Asp Gly Lys Phe Ala Ala Ala
            20                  25


<210> SEQ ID NO 9
<211> LENGTH: 10
<212> TYPE: PRT
<213> ORGANISM: Borrelia sp.

<400> SEQUENCE: 9

Pro Val Val Ala Glu Ser Pro Lys Lys Pro
1               5                   10


<210> SEQ ID NO 10
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (14)..(55)

<400> SEQUENCE: 10

atcagccgcc acc atg gac tac aag gac gac gat gac aag gga tct act        49
               Met Asp Tyr Lys Asp Asp Asp Asp Lys Gly Ser Thr
               1               5                   10

tcg aaa                                                               55
Ser Lys


<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Asp Tyr Lys Asp Asp Asp Asp Lys Gly Ser Thr Ser Lys
1               5                   10


<210> SEQ ID NO 12
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(54)

<400> SEQUENCE: 12

aaa aat gaa caa gga tcc gaa ttc aaa aag ctt ctc gag agt act tct       48
Lys Asn Glu Gln Gly Ser Glu Phe Lys Lys Leu Leu Glu Ser Thr Ser
1               5                   10                  15

aga gcg                                                               54
Arg Ala


<210> SEQ ID NO 13
```

-continued

<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Lys Asn Glu Gln Gly Ser Glu Phe Lys Lys Leu Leu Glu Ser Thr Ser
1 5 10 15

Arg Ala

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 14

His His His His His His
1 5

<210> SEQ ID NO 15
<211> LENGTH: 74
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 15

Met Lys Lys Asp Asp Gln Ile Ala Ala Ala Ile Ala Leu Arg Gly Met
1 5 10 15

Ala Lys Asp Gly Lys Phe Ala Val Lys Glu Leu Thr Ser Pro Val Val
20 25 30

Ala Glu Ser Pro Lys Lys Pro Met Lys Lys Asp Asp Gln Ile Ala Ala
35 40 45

Ala Met Val Leu Arg Gly Met Ala Lys Asp Gly Gln Phe Ala Leu Lys
50 55 60

Pro Val Val Ala Glu Ser Pro Lys Lys Pro
65 70

<210> SEQ ID NO 16
<211> LENGTH: 212
<212> TYPE: PRT
<213> ORGANISM: Borrelia afzelii

<400> SEQUENCE: 16

Met Lys Lys Asn Thr Leu Thr Ala Ile Leu Met Thr Leu Phe Leu Phe
1 5 10 15

Ile Ser Cys Asn Asn Ser Gly Lys Val Gly Ile Leu Thr Ser Thr Asn
20 25 30

Pro Ala Asp Glu Ser Ala Lys Gly Pro Asn Leu Thr Glu Ile Ser Lys
35 40 45

Lys Ile Thr Asp Ser Asn Ala Phe Val Leu Ala Val Lys Glu Val Glu
50 55 60

Thr Leu Val Leu Ser Ile Asp Glu Leu Ala Lys Lys Ala Ile Gly Gln
65 70 75 80

Lys Ile Asp Asn Asn Asn Gly Leu Ala Ala Leu Asn Asn Gln Asn Gly
85 90 95

```
Ser Leu Leu Ala Gly Ala Tyr Ala Ile Ser Thr Leu Ile Thr Glu Lys
            100                 105                 110

Leu Ser Lys Leu Lys Asn Leu Glu Glu Leu Lys Thr Glu Ile Ala Lys
        115                 120                 125

Ala Lys Lys Cys Ser Glu Glu Phe Thr Asn Lys Leu Lys Ser Gly His
    130                 135                 140

Ala Asp Leu Gly Lys Gln Asp Ala Thr Asp Asp His Ala Lys Ala Ala
145                 150                 155                 160

Ile Leu Lys Thr His Ala Thr Thr Asp Lys Gly Ala Lys Glu Phe Lys
                165                 170                 175

Asp Leu Phe Glu Ser Val Glu Gly Leu Leu Lys Ala Ala Gln Val Ala
            180                 185                 190

Leu Thr Asn Ser Val Lys Glu Leu Thr Ser Pro Val Val Ala Glu Ser
        195                 200                 205

Pro Lys Lys Pro
    210


<210> SEQ ID NO 17
<211> LENGTH: 210
<212> TYPE: PRT
<213> ORGANISM: Borrelia burgdorferi

<400> SEQUENCE: 17

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Asp Ser Asn Ala Val Leu Leu Ala Val Leu Glu Val Glu Ala
    50                  55                  60

Leu Leu Ser Ser Ile Asp Glu Ile Ala Ala Lys Ala Ile Gly Lys Lys
65                  70                  75                  80

Ile His Gln Asn Asn Gly Leu Asp Thr Glu Asn Asn His Asn Gly Ser
                85                  90                  95

Leu Leu Ala Gly Ala Tyr Ala Ile Ser Thr Leu Ile Lys Gln Lys Leu
            100                 105                 110

Asp Gly Leu Lys Asn Glu Gly Leu Lys Glu Lys Ile Asp Ala Ala Lys
        115                 120                 125

Lys Cys Ser Glu Thr Phe Thr Asn Lys Leu Lys Glu Lys His Thr Asp
    130                 135                 140

Leu Gly Lys Glu Gly Val Thr Asp Ala Asp Ala Lys Glu Ala Ile Leu
145                 150                 155                 160

Lys Thr Asn Gly Thr Lys Thr Lys Gly Ala Glu Glu Leu Gly Lys Leu
                165                 170                 175

Phe Glu Ser Val Glu Val Leu Ser Lys Ala Ala Lys Glu Met Leu Ala
            180                 185                 190

Asn Ser Val Lys Glu Leu Thr Ser Pro Val Val Ala Glu Ser Pro Lys
        195                 200                 205

Lys Pro
    210


<210> SEQ ID NO 18
<211> LENGTH: 209
<212> TYPE: PRT
```

<213> ORGANISM: Borrelia garinii

<400> SEQUENCE: 18

```
Met Lys Lys Asn Thr Leu Ser Ala Ile Leu Met Thr Leu Phe Leu Phe
1               5                   10                  15

Ile Ser Cys Asn Asn Ser Gly Gly Asp Thr Ala Ser Thr Asn Pro Asp
            20                  25                  30

Glu Ser Ala Lys Gly Pro Asn Leu Thr Val Ile Ser Lys Lys Ile Thr
        35                  40                  45

Asp Ser Asn Ala Phe Val Leu Ala Val Lys Glu Val Glu Ala Leu Ile
    50                  55                  60

Ser Ser Ile Asp Glu Leu Ala Asn Lys Ala Ile Gly Lys Val Ile His
65                  70                  75                  80

Gln Asn Asn Gly Leu Asn Ala Asn Ala Gly Gln Asn Gly Ser Leu Leu
                85                  90                  95

Ala Gly Ala Tyr Ala Ile Ser Thr Leu Ile Thr Glu Lys Leu Ser Lys
            100                 105                 110

Leu Lys Asn Ser Glu Glu Leu Asn Lys Lys Ile Glu Glu Ala Lys Asn
        115                 120                 125

His Ser Glu Ala Phe Thr Asn Arg Leu Lys Gly Ser His Ala Gln Leu
    130                 135                 140

Gly Val Ala Ala Ala Thr Asp Asp His Ala Lys Glu Ala Ile Leu Lys
145                 150                 155                 160

Ser Asn Pro Thr Lys Asp Lys Gly Ala Lys Glu Leu Lys Asp Leu Ser
                165                 170                 175

Glu Ser Val Glu Ser Leu Ala Lys Ala Ala Gln Glu Ala Leu Ala Asn
            180                 185                 190

Ser Val Lys Glu Leu Thr Asn Pro Val Val Ala Glu Ser Pro Lys Lys
        195                 200                 205

Pro
```

<210> SEQ ID NO 19
<211> LENGTH: 316
<212> TYPE: PRT
<213> ORGANISM: Borrelia burgdorferi

<400> SEQUENCE: 19

```
Ala Asn Leu Ser Lys Thr Gln Glu Lys Leu Ser Ser Gly Tyr Arg Ile
1               5                   10                  15

Asn Arg Ala Ser Asp Asp Ala Ala Gly Met Gly Val Ser Gly Lys Ile
            20                  25                  30

Asn Ala Gln Ile Arg Gly Leu Ser Gln Ala Ser Arg Asn Thr Ser Lys
        35                  40                  45

Ala Ile Asn Phe Ile Gln Thr Thr Glu Gly Asn Leu Asn Glu Val Glu
    50                  55                  60

Lys Val Leu Val Arg Met Lys Glu Leu Ala Val Gln Ser Gly Asn Gly
65                  70                  75                  80

Thr Tyr Ser Asp Ala Asp Arg Gly Ser Ile Gln Ile Glu Ile Glu Gln
                85                  90                  95

Leu Thr Asp Glu Ile Asn Arg Ile Ala Asp Gln Ala Gln Tyr Asn Gln
            100                 105                 110

Met His Met Leu Ser Asn Lys Ser Ala Ser Gln Asn Val Arg Thr Ala
        115                 120                 125

Glu Glu Leu Gly Met Gln Pro Ala Lys Ile Asn Thr Pro Ala Ser Leu
    130                 135                 140
```

```
Ser Gly Ser Gln Ala Ser Trp Thr Leu Arg Val His Val Gly Ala Asn
145                 150                 155                 160

Gln Asp Glu Ala Ile Ala Val Asn Ile Tyr Ala Ala Asn Val Ala Asn
                165                 170                 175

Leu Phe Ser Gly Glu Gly Ala Gln Thr Ala Gln Ala Ala Pro Val Gln
            180                 185                 190

Glu Gly Val Gln Gln Glu Gly Ala Gln Gln Pro Ala Pro Ala Thr Ala
        195                 200                 205

Pro Ser Gln Gly Gly Val Asn Ser Pro Val Asn Val Thr Thr Thr Val
    210                 215                 220

Asp Ala Asn Thr Ser Leu Ala Lys Ile Glu Asn Ala Ile Arg Met Ile
225                 230                 235                 240

Ser Asp Gln Arg Ala Asn Leu Gly Ala Phe Gln Asn Arg Leu Glu Ser
                245                 250                 255

Ile Lys Asn Ser Thr Glu Tyr Ala Ile Glu Asn Leu Lys Ala Ser Tyr
            260                 265                 270

Ala Gln Ile Lys Asp Ala Thr Met Thr Asp Glu Val Val Ala Ala Thr
        275                 280                 285

Thr Asn Ser Ile Leu Thr Gln Ser Ala Met Ala Met Ile Ala Gln Ala
    290                 295                 300

Asn Gln Val Pro Gln Tyr Val Leu Ser Leu Leu Arg
305                 310                 315


<210> SEQ ID NO 20
<211> LENGTH: 314
<212> TYPE: PRT
<213> ORGANISM: Borrelia burgdorferi

<400> SEQUENCE: 20

Ser Glu Ile Pro Lys Val Ser Leu Ile Ile Asp Gly Thr Phe Asp Asp
1               5                   10                  15

Lys Ser Phe Asn Glu Ser Ala Leu Asn Gly Val Lys Lys Val Lys Glu
            20                  25                  30

Glu Phe Lys Ile Glu Leu Val Leu Lys Glu Ser Ser Ser Asn Ser Tyr
        35                  40                  45

Leu Ser Asp Leu Glu Gly Leu Lys Asp Ala Gly Ser Asp Leu Ile Trp
    50                  55                  60

Leu Ile Gly Tyr Arg Phe Ser Asp Val Ala Lys Val Ala Ala Leu Gln
65                  70                  75                  80

Asn Pro Asp Met Lys Tyr Ala Ile Ile Asp Pro Ile Tyr Ser Asn Asp
                85                  90                  95

Pro Ile Pro Ala Asn Leu Val Gly Met Thr Phe Arg Ala Gln Glu Gly
            100                 105                 110

Ala Phe Leu Thr Gly Tyr Ile Ala Ala Lys Leu Ser Lys Thr Gly Lys
        115                 120                 125

Ile Gly Phe Leu Gly Gly Ile Glu Gly Glu Ile Val Asp Ala Phe Arg
    130                 135                 140

Tyr Gly Tyr Glu Ala Gly Ala Lys Tyr Ala Asn Lys Asp Ile Lys Ile
145                 150                 155                 160

Ser Thr Gln Tyr Ile Gly Ser Phe Ala Asp Leu Glu Ala Gly Arg Ser
                165                 170                 175

Val Ala Thr Arg Met Tyr Ser Asp Glu Ile Asp Ile Ile His His Ala
            180                 185                 190

Ala Gly Leu Gly Gly Ile Gly Ala Ile Glu Val Ala Lys Glu Leu Gly
```

```
        195                 200                 205

Ser Gly His Tyr Ile Ile Gly Val Asp Glu Asp Gln Ala Tyr Leu Ala
    210                 215                 220

Pro Asp Asn Val Ile Thr Ser Thr Thr Lys Asp Val Gly Arg Ala Leu
225                 230                 235                 240

Asn Ile Phe Thr Ser Asn His Leu Lys Thr Asn Thr Phe Glu Gly Gly
                245                 250                 255

Lys Leu Ile Asn Tyr Gly Leu Lys Glu Gly Val Val Gly Phe Val Arg
            260                 265                 270

Asn Pro Lys Met Ile Ser Phe Glu Leu Glu Lys Glu Ile Asp Asn Leu
        275                 280                 285

Ser Ser Lys Ile Ile Asn Lys Glu Ile Ile Val Pro Ser Asn Lys Glu
    290                 295                 300

Ser Tyr Glu Lys Phe Leu Lys Glu Phe Ile
305                 310


<210> SEQ ID NO 21
<211> LENGTH: 156
<212> TYPE: PRT
<213> ORGANISM: Borrelia burgdorferi

<400> SEQUENCE: 21

Ala Leu Glu Ser Ser Ser Lys Asp Leu Lys Asn Lys Ile Leu Lys Ile
1               5                   10                  15

Lys Lys Asp Ala Thr Gly Lys Gly Val Leu Phe Glu Ala Phe Thr Gly
            20                  25                  30

Leu Lys Thr Gly Ser Lys Val Thr Ser Gly Gly Leu Ala Leu Arg Glu
        35                  40                  45

Ala Lys Val Gln Ala Ile Val Glu Thr Gly Lys Phe Leu Lys Ile Ile
    50                  55                  60

Glu Glu Glu Ala Leu Lys Leu Lys Glu Thr Gly Asn Ser Gly Gln Phe
65                  70                  75                  80

Leu Ala Met Phe Asp Leu Met Leu Glu Val Val Glu Ser Leu Glu Asp
                85                  90                  95

Val Gly Ile Ile Gly Leu Lys Ala Arg Val Leu Glu Glu Ser Lys Asn
            100                 105                 110

Asn Pro Ile Asn Thr Ala Glu Arg Leu Leu Ala Ala Lys Ala Gln Ile
        115                 120                 125

Glu Asn Gln Leu Lys Val Val Lys Glu Lys Gln Asn Ile Glu Asn Gly
    130                 135                 140

Gly Glu Lys Lys Asn Asn Lys Ser Lys Lys Lys Lys
145                 150                 155


<210> SEQ ID NO 22
<211> LENGTH: 162
<212> TYPE: PRT
<213> ORGANISM: Borrelia burgdorferi

<400> SEQUENCE: 22

Glu Thr Lys Ile Ile Leu Glu Arg Ser Ala Lys Asp Ile Ile Asp Glu
1               5                   10                  15

Ile Asn Lys Ile Lys Lys Asp Ala Ala Asp Asn Asn Val Asn Phe Ala
            20                  25                  30

Ala Phe Lys Glu Asp Lys Thr Gly Ser Lys Val Ser Glu Asn Ser Phe
        35                  40                  45

Ile Leu Glu Ala Lys Met Arg Gly Thr Thr Val Ala Glu Lys Phe Val
```

```
    50                  55                  60

Thr Ala Ile Glu Gly Glu Ala Thr Lys Leu Lys Lys Thr Gly Ser Ser
65                  70                  75                  80

Gly Glu Phe Ser Ala Met Tyr Asn Met Met Leu Glu Val Ser Gly Pro
                85                  90                  95

Leu Glu Glu Leu Gly Val Leu Arg Met Thr Lys Thr Val Thr Asp Ala
            100                 105                 110

Ala Glu Gln His Pro Thr Thr Thr Ala Glu Gly Ile Leu Glu Ile Ala
        115                 120                 125

Lys Thr Met Lys Thr Lys Leu Gln Arg Val His Thr Lys Asn Tyr Cys
    130                 135                 140

Ala Leu Lys Lys Lys Glu Asn Pro Ser Phe Thr Asp Glu Lys Cys Lys
145                 150                 155                 160

Asn Asn


<210> SEQ ID NO 23
<211> LENGTH: 189
<212> TYPE: PRT
<213> ORGANISM: Borrelia burgdorferi

<400> SEQUENCE: 23

Ser Gly Lys Asp Gly Asn Thr Ser Ala Asn Ser Ala Asp Glu Ser Val
1               5                   10                  15

Lys Gly Pro Asn Leu Thr Glu Ile Ser Lys Lys Ile Thr Asp Ser Asn
            20                  25                  30

Ala Val Leu Leu Ala Val Lys Glu Val Glu Ala Leu Leu Ser Ser Ile
        35                  40                  45

Asp Glu Ile Ala Ala Lys Ala Ile Gly Lys Lys Ile His Gln Asn Asn
    50                  55                  60

Gly Leu Asp Thr Glu Asn Asn His Asn Gly Ser Leu Leu Ala Gly Ala
65                  70                  75                  80

Tyr Ala Ile Ser Thr Leu Ile Lys Gln Lys Leu Asp Gly Leu Lys Asn
                85                  90                  95

Glu Gly Leu Lys Glu Lys Ile Asp Ala Ala Lys Lys Cys Ser Glu Thr
            100                 105                 110

Phe Thr Asn Lys Leu Lys Glu Lys His Thr Asp Leu Gly Lys Glu Gly
        115                 120                 125

Val Thr Asp Ala Asp Ala Lys Glu Ala Ile Leu Lys Thr Asn Gly Thr
    130                 135                 140

Lys Thr Lys Gly Ala Glu Glu Leu Gly Lys Leu Phe Glu Ser Val Glu
145                 150                 155                 160

Val Leu Ser Lys Ala Ala Lys Glu Met Leu Ala Asn Ser Val Lys Glu
                165                 170                 175

Leu Thr Ser Pro Val Val Ala Glu Ser Pro Lys Lys Pro
            180                 185


<210> SEQ ID NO 24
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Asp Ala Ala Glu Gln Asp Gly Lys Lys Pro Glu Glu Ala Lys Asn
1               5                   10                  15
```

```
Pro Ile Ala Ala Ala Ile Gly Asp Lys Asp Gly Asp Ala Glu Phe Asn
            20                  25                  30

Gln Asp Asp Met Lys Lys Asp Asp Gln Ile Ala Ala Ala Ile Ala Leu
        35                  40                  45

Arg Gly Met Ala Lys Asp Gly Lys
    50                  55


<210> SEQ ID NO 25
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

gccgacgccg ccgagcagga cggcaagaag cccgaggagg ccaagaaccc catcgccgcc      60

gccatcggcg acaaggacgg cgacgccgag ttcaaccagg acgacatgaa gaaggacgac     120

cagatcgccg ccgccatcgc cctgcgcggc atggctaagg atggaaagtg a              171


<210> SEQ ID NO 26
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Ala Gly Lys Leu Phe Gly Lys Ala Gly Ala Ala Ala His Gly Asp
1               5                   10                  15

Ser Glu Ala Ala Ser Lys Ala Ala Gly Ala Val Ser Ala Val Ser Gly
            20                  25                  30

Glu Gln Ile Leu Ser Ala Ile Val Thr Ala Ala Asp Ala Ala Glu Gln
        35                  40                  45

Asp Gly Lys Lys Pro Glu Glu Ala Lys Asn Pro Ile Ala Ala Ala Ile
    50                  55                  60

Gly Asp Lys Asp Gly Gly Ala Glu Phe Gly Gln Asp Glu Met Lys Lys
65                  70                  75                  80

Asp Asp Gln Ile Ala Ala Ala Ile Ala Leu Arg Gly Met Ala Lys Asp
                85                  90                  95

Gly Lys Phe Ala Val Lys Asp Gly Glu Lys Glu Lys Ala Glu Gly Ala
            100                 105                 110

Ile Lys Gly Ala Ala Glu Ser Ala Val Arg Lys Val Leu Gly Ala Ile
        115                 120                 125

Thr Gly Leu Ile Gly Asp Ala Val Ser Ser Gly Leu Arg Lys Val Gly
    130                 135                 140

Asp Ser Val Lys Ala Ala Ser Lys Glu Thr Pro Pro Ala Leu Asn Lys
145                 150                 155                 160


<210> SEQ ID NO 27
<211> LENGTH: 483
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
```

-continued ggtgccggta agttgttcgg taaggctggt gccgcagcac acggtgatag tgaagccgcc 60
tccaaggctg ccggtgctgt aagcgctgtc tccggtgaac aaatcttgtc cgctatagtt 120
accgctgccg atgcagctga acaagatggt aaaaagccag aagaagcaaa gaatcccatt 180
gctgctgcaa ttggtgataa ggatggtggt gccgaatttg gtcaagatga aatgaaaaag 240
gatgatcaaa tcgcagccgc catcgccctt cgcggtatgg ccaaagatgg taaatttgca 300
gttaaggatg gtgaaaaaga aaaagctgaa ggcgcaatta agggtgccgc tgaaagcgcc 360
gtacgcaagg tactcggtgc aattacgggt ctcattggtg atgcagtgag ctcaggtctg 420
cgcaaggtgg gtgatagtgt gaaagctgcc agcaaagaaa cacccccgc cctcaacaag 480 tag 483

<210> SEQ ID NO 28
<211> LENGTH: 192
<212> TYPE: PRT
<213> ORGANISM: Borrelia burgdorferi

<400> SEQUENCE: 28

Glu Gly Ala Ile Lys Glu Val Ser Glu Leu Leu Asp Lys Leu Val Lys
1 5 10 15

Ala Val Lys Thr Ala Glu Gly Ala Ser Ser Gly Thr Ala Ala Ile Gly
20 25 30

Glu Val Val Ala Asp Ala Asp Ala Ala Lys Val Ala Asp Lys Ala Ser
35 40 45

Val Lys Gly Ile Ala Lys Gly Ile Lys Glu Ile Val Glu Ala Ala Gly
50 55 60

Gly Ser Glu Lys Leu Lys Ala Val Ala Ala Ala Lys Gly Glu Asn Asn
65 70 75 80

Lys Gly Ala Gly Lys Leu Phe Gly Lys Ala Gly Ala Ala Ala His Ala
85 90 95

Gly Asp Ser Glu Ala Ala Ser Lys Ala Ala Gly Ala Val Ser Ala Val
100 105 110

Ser Gly Glu Gln Ile Leu Ser Ala Ile Val Thr Ala Ala Asp Ala Ala
115 120 125

Glu Gln Glu Gly Lys Lys Pro Ala Glu Ala Lys Asn Pro Ile Ala Ala
130 135 140

Ala Ile Gly Asn Lys Asp Gly Gly Ala Glu Phe Gly Gln Asp Glu Met
145 150 155 160

Lys Lys Asp Asp Gln Ile Ala Ala Ala Ile Ala Leu Arg Gly Met Ala
165 170 175

Lys Asp Gly Lys Phe Ala Val Lys Glu Asp Asn Lys Lys Gly Lys Ala
180 185 190

<210> SEQ ID NO 29
<211> LENGTH: 576
<212> TYPE: DNA
<213> ORGANISM: Borrelia burgdorferi

<400> SEQUENCE: 29
gagggggcta ttaaggaagt tagcgagttg ttggataagc tggtaaaagc tgtaaagaca 60
gctgaggggg cttcaagtgg tactgctgca attggagaag ttgtggctga tgctgatgct 120
gcaaaggttg ctgataaggc gagtgtgaag ggattgcta aggggataaa ggagattgtt 180
gaagctgctg gggggagtga aaagctgaaa gctgttgctg ctgctaaagg ggagaataat 240 aaagggcag ggaagttgtt tgggaaggct ggtgctgctg ctcatgctgg ggacagtgag 300

-continued

```
gctgctagca aggcggctgg tgctgttagt gctgttagtg gggagcagat attaagtgcg    360

attgttacgg ctgctgatgc ggctgagcag gagggaaaga agcctgcaga ggctaaaaat    420

ccgattgctg ctgctattgg gaataaagat gggggtgcgg agtttggtca ggatgagatg    480

aagaaggatg atcagattgc tgctgctatt gctttgaggg ggatggctaa ggatggaaag    540

tttgctgtga aggaggataa taagaaaggg aaggct                              576


<210> SEQ ID NO 30
<211> LENGTH: 174
<212> TYPE: PRT
<213> ORGANISM: Borrelia garinii

<400> SEQUENCE: 30

Ala Ser Ala Ala Thr Gly Asn Ala Ala Ile Gly Asp Val Val Asn Gly
1               5                   10                  15

Asp Val Ala Lys Ala Lys Gly Gly Asp Ala Ala Ser Val Asn Gly Ile
            20                  25                  30

Ala Lys Gly Ile Lys Gly Ile Val Asp Ala Ala Glu Lys Ala Asp Ala
        35                  40                  45

Lys Glu Gly Lys Leu Asn Ala Ala Gly Ala Glu Gly Thr Thr Asn Ala
    50                  55                  60

Asp Ala Gly Lys Leu Phe Val Lys Asn Ala Gly Asn Val Gly Gly Glu
65                  70                  75                  80

Ala Gly Asp Ala Gly Lys Ala Ala Ala Ala Val Ala Ala Val Ser Gly
                85                  90                  95

Glu Gln Ile Leu Lys Ala Ile Val Asp Ala Ala Lys Asp Gly Gly Glu
            100                 105                 110

Lys Gln Gly Lys Lys Ala Ala Asp Ala Thr Asn Pro Ile Asp Ala Ala
        115                 120                 125

Ile Gly Gly Thr Asn Asp Asn Asp Ala Ala Ala Ala Phe Ala Thr Met
    130                 135                 140

Lys Lys Asp Asp Gln Ile Ala Ala Ala Met Val Leu Arg Gly Met Ala
145                 150                 155                 160

Lys Asp Gly Gln Phe Ala Leu Lys Asp Ala Ala Ala Ala His
                165                 170


<210> SEQ ID NO 31
<211> LENGTH: 522
<212> TYPE: DNA
<213> ORGANISM: Borrelia garinii

<400> SEQUENCE: 31

gcaagtgctg ctactggtaa tgcagcgatt ggagatgttg ttaatggtga tgtggcaaaa     60

gcaaaaggtg gtgatgcggc gagtgttaat gggattgcta aggggataaa ggggattgtt    120

gatgctgctg agaaggctga tgcgaaggaa gggaagttga atgctgctgg tgctgagggt    180

acgactaacg cggatgctgg gaagttgttt gtgaagaatg ctggtaatgt gggtggtgaa    240

gcaggtgatg ctgggaaggc tgctgctgcg gttgctgctg ttagtgggga gcagatatta    300

aaagcgattg ttgatgctgc taaggatggt ggtgagaagc agggtaagaa ggctgcggat    360

gctacaaatc cgattgacgc ggctattggg ggtacaaatg ataatgatgc tgctgcggcg    420

tttgctacta tgaagaagga tgatcagatt gctgctgcta tggttctgag gggaatggct    480

aaggatgggc aatttgcttt gaaggatgct gctgctgctc at                       522
```

-continued

<210> SEQ ID NO 32
<211> LENGTH: 202
<212> TYPE: PRT
<213> ORGANISM: Borrelia afzelii

<400> SEQUENCE: 32

```
Glu Ser Ala Val Asp Gly Val Ser Lys Trp Leu Glu Glu Met Ile Lys
1               5                   10                  15

Ala Ala Lys Glu Ala Ala Thr Lys Gly Gly Thr Gly Gly Gly Ser Glu
            20                  25                  30

Lys Ile Gly Asp Val Gly Ala Ala Asn Asn Gln Gly Ala Val Ala Asp
        35                  40                  45

Lys Asp Ser Val Lys Gly Ile Ala Lys Gly Ile Lys Gly Ile Val Asp
    50                  55                  60

Ala Ala Gly Lys Ala Phe Gly Lys Asp Gly Asn Ala Leu Thr Gly Val
65                  70                  75                  80

Lys Glu Val Ala Asp Glu Ala Gly Ala Asn Glu Asp Ala Gly Lys Leu
                85                  90                  95

Phe Ala Gly Asn Ala Gly Asn Ala Ala Ala Asp Ile Ala Lys Ala
            100                 105                 110

Ala Gly Ala Val Thr Ala Val Ser Gly Glu Gln Ile Leu Lys Ala Ile
        115                 120                 125

Val Asp Gly Ala Gly Gly Ala Ala Gln Asp Gly Lys Lys Ala Ala Glu
    130                 135                 140

Ala Lys Asn Pro Ile Ala Ala Ala Ile Gly Ala Asp Ala Ala Gly Ala
145                 150                 155                 160

Asp Phe Gly Asp Asp Met Lys Lys Ser Asp Lys Ile Ala Ala Ala Ile
                165                 170                 175

Val Leu Arg Gly Val Ala Lys Ser Gly Lys Phe Ala Val Ala Asn Ala
            180                 185                 190

Ala Lys Lys Glu Ser Val Lys Ser Ala Val
        195                 200
```

<210> SEQ ID NO 33
<211> LENGTH: 606
<212> TYPE: DNA
<213> ORGANISM: Borrelia afzelii

<400> SEQUENCE: 33

```
gagagtgctg ttgatggggt tagcaagtgg ttagaagaga tgataaaagc tgctaaggag      60

gctgctacaa agggtggtac tggtggtggt agcgaaaaga ttggggatgt tggtgctgct     120

aataatcagg gtgctgtagc tgataaggac agtgttaagg ggattgcgaa ggggataaag     180

gggattgttg atgctgctgg gaaggctttt ggtaaggatg gtaatgcgct gacaggtgta     240

aaagaagttg ctgatgaggc tggggctaac gaggatgcgg ggaagttgtt tgctggtaat     300

gctggtaatg ctgctgctgc tgacattgcg aaggcggctg gtgctgttac tgcggttagt     360

ggggagcaga tactgaaagc tattgttgat ggtgctggtg gtgcggctca agatggtaaa     420

aaggctgcgg aggctaagaa tccgattgca gctgcgattg gggctgatgc tgctggtgcg     480

gattttggtg atgatatgaa gaagagtgat aagattgctg cggctattgt tttgaggggg     540

gtggctaaga gtggaaagtt tgctgttgct aatgctgcta agaaggagag tgtgaagagt     600

gctgtg                                                                606
```